US011958052B2

(12) United States Patent
Sekizawa et al.

(10) Patent No.: US 11,958,052 B2
(45) Date of Patent: Apr. 16, 2024

(54) THERMOCYCLING INSPECTION DEVICE AND CHIP HOLDER

(71) Applicant: METABOSCREEN CO., LTD., Yokohama (JP)

(72) Inventors: Ryuichi Sekizawa, Yokohama (JP); Ryoko Aso, Yokohama (JP); Hiroshi Mitsutake, Yokohama (JP)

(73) Assignee: METABOSCREEN CO., LTD., Yokohama (JP)

( * ) Notice: Subject to any disclaimer, the term of this patent is extended or adjusted under 35 U.S.C. 154(b) by 510 days.

(21) Appl. No.: 16/091,788

(22) PCT Filed: Apr. 6, 2017

(86) PCT No.: PCT/JP2017/014418
§ 371 (c)(1),
(2) Date: Oct. 5, 2018

(87) PCT Pub. No.: WO2017/175841
PCT Pub. Date: Oct. 12, 2017

(65) Prior Publication Data
US 2019/0099757 A1    Apr. 4, 2019

(30) Foreign Application Priority Data

Apr. 7, 2016  (JP) ................. 2016-077655

(51) Int. Cl.
*B01L 7/00* (2006.01)
*C12M 1/00* (2006.01)
(Continued)

(52) U.S. Cl.
CPC .............. *B01L 7/52* (2013.01); *C12M 1/00* (2013.01); *G01N 1/42* (2013.01); *G01N 1/44* (2013.01);
(Continued)

(58) Field of Classification Search
CPC ...... B01L 7/52; B01L 2200/147; B01L 9/527; B01L 3/502715; B01L 2300/0654;
(Continued)

(56) References Cited

U.S. PATENT DOCUMENTS 6,337,435 B1 *  1/2002  Chu ..................... B01L 7/52
                                             136/203
2006/0101830 A1 *  5/2006  Cohen ............... B01L 3/50851
                                             62/3.3

(Continued)

FOREIGN PATENT DOCUMENTS

JP    2002-126494 A    5/2002
JP    2011-203181 A    10/2011
(Continued)

OTHER PUBLICATIONS

International Search Report for International Application No. PCT/JP2017/014418 dated Jul. 4, 2017 (2 sheets).

*Primary Examiner* — Liban M Hassan
(74) *Attorney, Agent, or Firm* — Kratz, Quintos & Hanson, LLP

(57) ABSTRACT

The thermocycling inspection device includes a holder-accommodating space 10 for accommodating the chip holder 50 therein, a thermocycling section 20 for heating and cooling the inspection chip 60, and a detector 30 for taking a picture of the inspection chip 60, and when the thermocycling section 20 heats or cools or when a picture is taken by the detector 30, the thermocycling section 20 is disposed on one side of the holder-accommodating space 10, the detector 30 is disposed on other side of the holder-accommodating space 10, and the holder-accommodating space 10 is formed such that an optical axis of the detector 30 and a sample introducing port 62 match with each other. According to this, polymerase chain reaction can be carried out, and (Continued)

inspection can be carried out using the inspection chip which carries out the polymerase chain reaction.

5 Claims, 15 Drawing Sheets

(51) Int. Cl.
| | |
|---|---|
| *G01N 1/42* | (2006.01) |
| *G01N 1/44* | (2006.01) |
| *G01N 21/64* | (2006.01) |
| *G01N 21/84* | (2006.01) |
| *B01L 3/00* | (2006.01) |
| *B01L 9/00* | (2006.01) |
| *C12Q 1/686* | (2018.01) |

(52) U.S. Cl.
CPC ....... *G01N 21/6428* (2013.01); *G01N 21/645* (2013.01); *G01N 21/6456* (2013.01); *G01N 21/8483* (2013.01); *B01L 3/502715* (2013.01); *B01L 9/527* (2013.01); *B01L 2200/025* (2013.01); *B01L 2200/142* (2013.01); *B01L 2200/147* (2013.01); *B01L 2300/0609* (2013.01); *B01L 2300/0636* (2013.01); *B01L 2300/0654* (2013.01); *B01L 2300/0819* (2013.01); *B01L 2300/0861* (2013.01); *B01L 2300/1822* (2013.01); *B01L 2400/0406* (2013.01); *C12Q 1/686* (2013.01)

(58) Field of Classification Search
CPC ......... B01L 2200/025; B01L 2200/142; B01L 2300/0609; B01L 2300/0636; B01L 2300/0819; B01L 2300/0861; B01L 2300/1822; B01L 2400/0406; B01L 2200/0663; B01L 2300/0627; G01N 21/645; G01N 21/8483; G01N 1/42; G01N 1/44; G01N 21/6428; G01N 21/6456; G01N 35/00029; G01N 2035/00366; G01N 2035/00158; C12M 1/00; C12Q 1/686; C12Q 1/68
USPC ........................................ 435/287.2, 289.1
See application file for complete search history.

(56) References Cited

U.S. PATENT DOCUMENTS

| | | | |
|---|---|---|---|
| 2010/0240044 A1* | 9/2010 | Kumar | ...................... B01L 7/52 |
| | | | 435/6.11 |
| 2010/0240051 A1* | 9/2010 | Wang | ................ B01L 3/502715 |
| | | | 435/6.11 |
| 2012/0052560 A1 | 3/2012 | Knight | |
| 2012/0171678 A1* | 7/2012 | Maltezos | ................... B01L 7/52 |
| | | | 435/6.12 |
| 2012/0184025 A1 | 7/2012 | Kawata | |
| 2013/0078610 A1* | 3/2013 | Kimball | ................. C12P 19/34 |
| | | | 435/3 |
| 2013/0101993 A1* | 4/2013 | Sekizawa | .................. G01N 1/28 |
| | | | 435/5 |
| 2013/0331298 A1* | 12/2013 | Rea | ...................... C12Q 1/6844 |
| | | | 506/16 |

FOREIGN PATENT DOCUMENTS

| | | |
|---|---|---|
| JP | 2013-224960 A | 10/2013 |
| JP | 2013-544490 A | 12/2013 |
| JP | 2014-010109 A | 1/2014 |
| WO | 2011/040504 A1 | 4/2011 |
| WO | 2012/001972 A1 | 1/2012 |

* cited by examiner

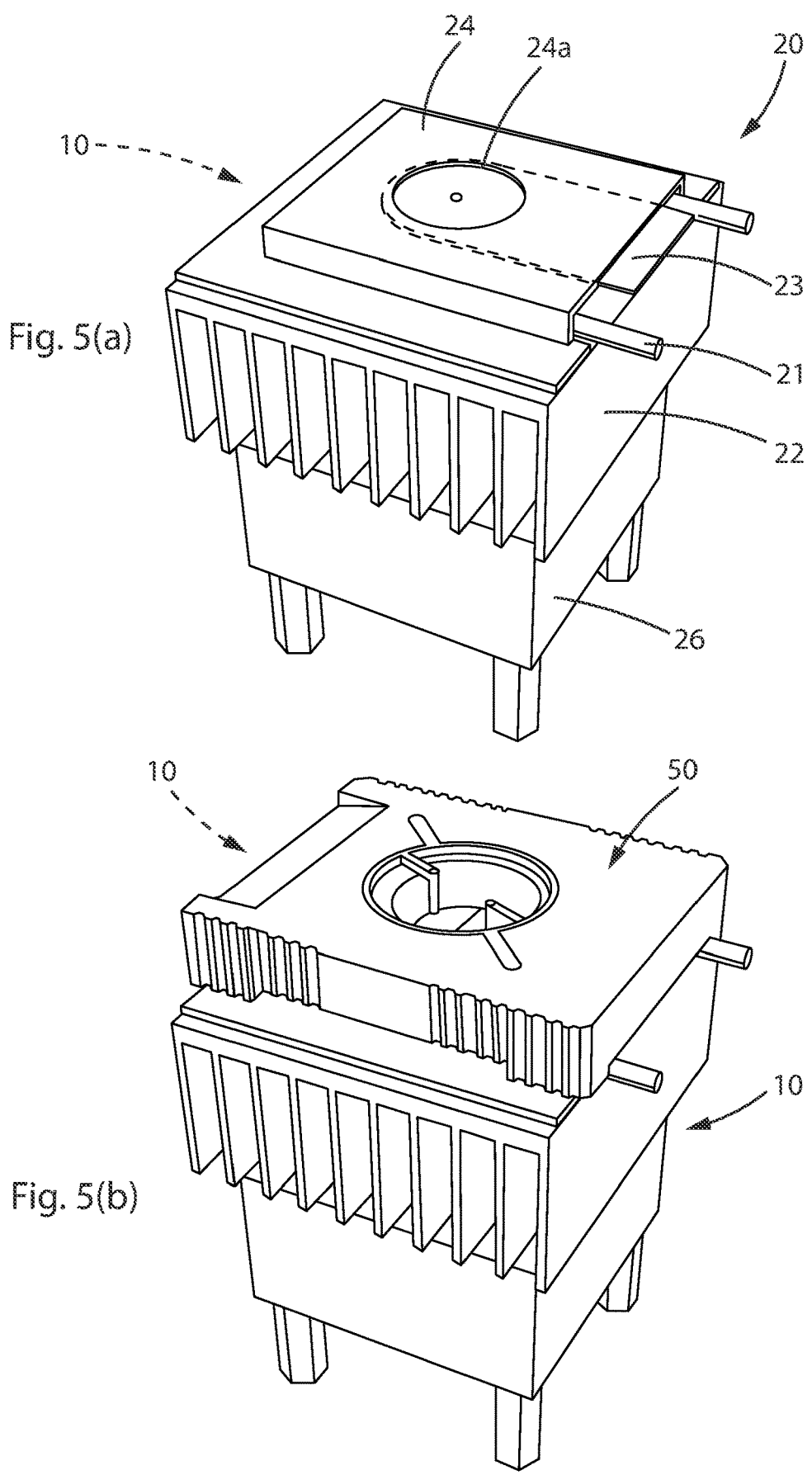

Fig. 8
(a) 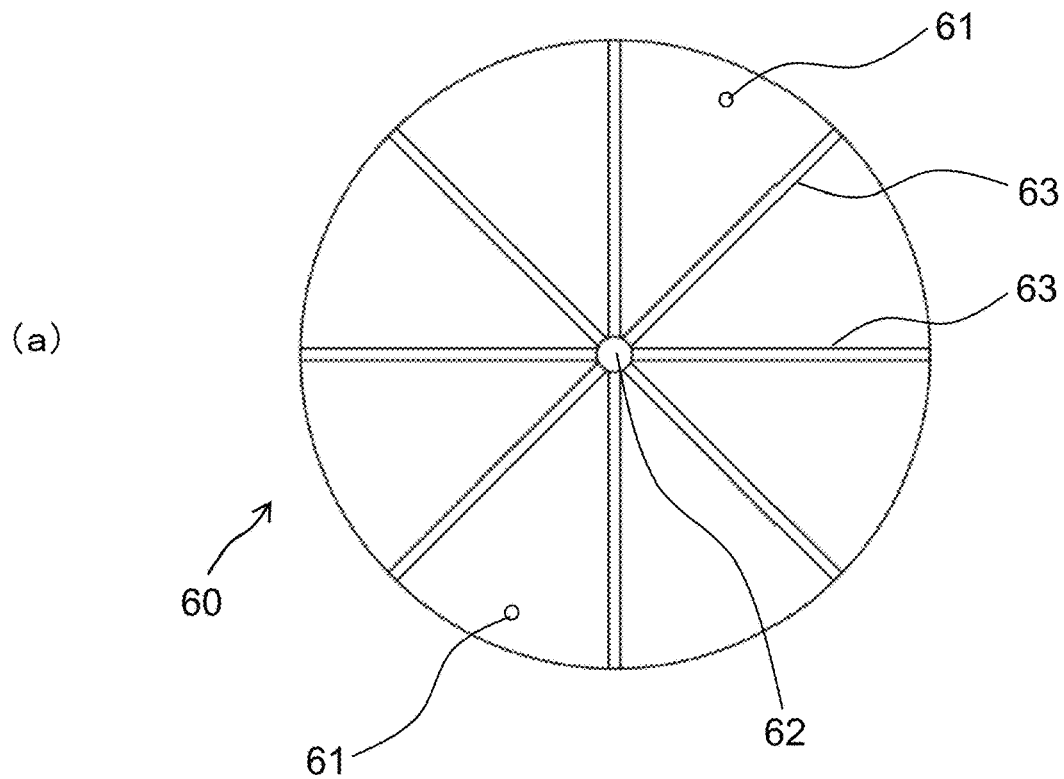
(b) 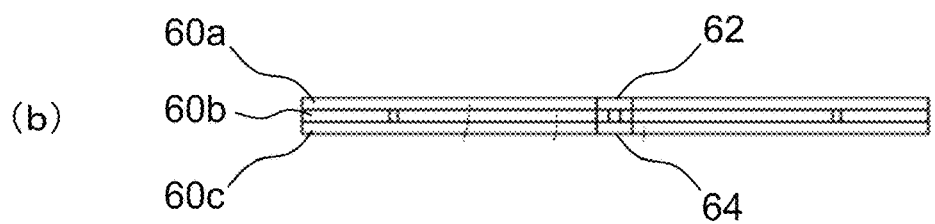
(c) 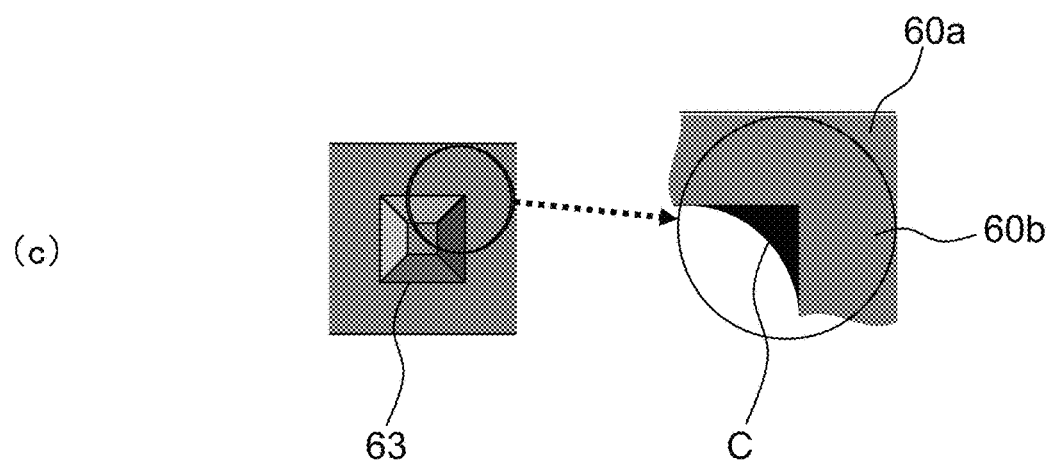

THERMOCYCLING INSPECTION DEVICE AND CHIP HOLDER

TECHNICAL FIELD

The present invention relates to a thermocycling inspection device for inspecting a specimen by means of polymerase chain reaction using a chip holder, and the invention also relates to the chip holder used for the thermocycling inspection device.

BACKGROUND TECHNIQUE

As an inspection chip of this kind, there is proposed one in which a through hole-shaped flow passage is formed therein, a capillary is embedded in at least a portion of the flow passage, a dummy rod which is for closing the flow passage is further embedded, the flow passage is shaped into a branch form or a lattice form, and the capillary is made of glass or plastic (patent document 1).

As another inspection chip, there is proposed one in which a plurality of grooves connected onto a substrate in parallel or in series are formed, capillaries which are chemically modified in a mutually different manner are respectively embedded in the plurality of grooves, fluid is supplied to these plurality of embedded capillaries, and detection data is acquired (patent document 2).

There is also proposed an inspection chip capable of producing, in a simple fashion, a sample flow passage which is a square hollow groove, and one of sides of the square shape has an angle of about 100 microns. In this inspection chip, sample solution can easily be introduced into the sample flow passage, and a plurality kinds of micro chemical reaction fields can be carried out at the same time using one inspection chip (patent document 3).

Patent documents 4 to 7 further disclose structures and producing methods of other inspection chips.

PRIOR ART DOCUMENTS

Patent Documents

[Patent Document 1]
  Japanese Patent Publication No. 4073023
[Patent Document 2]
  Japanese Utility Model Registration No. 3116709
[Patent Document 3]
  WO2012/001972
[Patent Document 4]
  Japanese Patent Application Laid-open No. 2000-93816
[Patent Document 5]
  Japanese Patent Application Laid-open No. 2001-157855
[Patent Document 6]
  Japanese Patent Application Laid-open No. 2000-81406
[Patent Document 7]
  Japanese Translation of PCT international Application Publication No. 2005-510695

SUMMARY OF THE INVENTION

Problem to be Solved by the Invention

In small space reaction using an inspection chip, it is possible not only to achieve a trace amount of a sample to be used, but also to enhance speed and efficiency of reaction. However, in order to utilize this feature, it is necessary to provide a thermocycling inspection device capable of using this inspection chip.

Thereupon, it is an object of the present invention to provide a thermocycling inspection device and a chip holder capable of carrying out polymerase chain reaction, and capable of carrying out inspection using an inspection chip which carried out the polymerase chain reaction.

Means for Solving the Problem

A first aspect of the present invention provides a thermocycling inspection device in which a sample introducing port is formed in a central portion of an inspection chip, and a plurality of sample flow passages which radially extend from the sample introducing port are formed in the inspection chip, the inspection chip which fixes reagent to the sample flow passages is accommodated in a chip holder, and a specimen is inspected by polymerase chain reaction using the chip holder, wherein thermocycling inspection device includes a holder-accommodating space for accommodating the chip holder therein, a thermocycling section for heating and cooling the inspection chip, and a detector for taking a picture of the inspection chip, and when the thermocycling section heats or cools or when a picture is taken by the detector, the thermocycling section is disposed on one side of the holder-accommodating space, the detector is disposed on other side of the holder-accommodating space, and the holder-accommodating space is formed such that an optical axis of the detector and the sample introducing port match with each other.

According to a second aspect of the invention, in the thermocycling inspection device described in the first aspect, the thermocycling section includes a Peltier element, a heat sink disposed on one of surfaces of the Peltier element, a surface heater disposed on other surface of the Peltier element, and a cover plate which covers the surface heater and the other surface of the Peltier element, the holder-accommodating space is formed such that it covers the cover plate, an opening capable of abutting a chip-accommodating saucer of the chip holder against the surface heater is formed in the cover plate, and the inspection chip accommodated in the chip-accommodating saucer is heated by the surface heater.

According to a third aspect of the invention, in the thermocycling inspection device described in the second aspect, a temperature sensor is disposed between the surface heater and the chip-accommodating saucer.

According to a fourth aspect of the invention, in the thermocycling inspection device described in the second aspect, the thermocycling inspection device further comprises a holder-pressing lid which covers the chip holder disposed in the holder-accommodating space, wherein a fluorescence detection window is formed in the holder-pressing lid, a transparent substrate is provided on the holder-pressing lid on a side of the holder-accommodating space, and the transparent substrate covers the fluorescence detection window and presses the chip holder.

According to a fifth aspect of the invention, in the thermocycling inspection device described in the first aspect, the thermocycling section includes a Peltier element, a surface heater, a temperature sensor for detecting temperature of the inspection chip, and a control section for controlling temperature of the Peltier element and the surface heater, the surface heater heats the inspection chip, the Peltier element cools the surface heater, and the control section controls the surface heater and the Peltier element such that detection temperature detected by the temperature sensor is cyclically repeated between first set temperature and second set temperature which is lower than the first set temperature.

According to a sixth aspect of the invention, in the thermocycling inspection device described in the fifth aspect, when the detection temperature detected by the temperature sensor detects the first set temperature, the control section turns the surface heater OFF and turns the Peltier element ON.

According to a seventh aspect of the invention, in the thermocycling inspection device described in the fifth aspect, when the detection temperature detected by the temperature sensor detects the second set temperature, the control section feedback controls the surface heater such that the detection temperature becomes equal to the second set temperature in a state where the Peltier element is OFF, thereby maintaining the second set temperature for predetermined time.

According to an eighth aspect of the invention, in the chip holder used for the thermocycling inspection device described in the first aspect, the chip holder comprises a chip-accommodating saucer for accommodating the inspection chip therein, a holder for holding the chip-accommodating saucer at a central portion of the holder, and a chip-pressing material for pressing the inspection chip accommodated in the chip-accommodating saucer against the chip-accommodating saucer, and the chip-pressing material is positioned by the holder.

A ninth aspect of the invention provides an inspection chip which is formed by a sample introducing port formed in a central portion of the inspection chip, and a plurality of sample flow passages radially extending from the sample introducing port, the chip holder accommodates the inspection chip which fixes reagent to the sample flow passages, the chip holder further includes a chip-accommodating saucer for accommodating the inspection chip therein, a holder for holding the chip-accommodating saucer at a central portion of the holder, and a chip-pressing material for pressing the inspection chip accommodated in the chip-accommodating saucer against the chip-accommodating saucer and the chip-pressing material is positioned by the holder.

According to a tenth aspect of the invention, in the chip holder described in the ninth aspect, a positioning projection is formed on the chip-accommodating saucer, and a positioning recess corresponding to the positioning projection is formed in the inspection chip.

According to an eleventh aspect of the invention, in the chip holder described in the ninth aspect, the chip-accommodating saucer is made of material having higher thermal conductivity than the holder.

According to a twelfth aspect of the invention, in the chip holder described in the ninth aspect, a recess is provided in a central portion of the chip-accommodating saucer.

According to a thirteenth aspect of the invention, the chip holder described in the ninth aspect further comprises a transparent film which is attached to the holder to prevent oil added to the chip-accommodating saucer from overflowing.

A fourteenth aspect of the invention provides a thermocycling inspection device comprising a holder-accommodating space for accommodating a chip holder therein, a thermocycling section for heating and cooling an inspection chip, a detector for taking a picture of the inspection chip, and a holder-pressing lid which covers the chip holder disposed in the holder-accommodating space, wherein the thermocycling section includes a Peltier element, a heat sink disposed on one of surfaces of the Peltier element, a surface heater disposed on other surface of the Peltier element, and a cover plate which covers the surface heater and the other surface of the Peltier element, the holder-accommodating space is formed to cover the cover plate, an opening is formed in the cover plate, and a fluorescence detection window for taking a picture of the inspection chip by the detector is formed in the holder-pressing lid.

A fifteenth aspect of the invention provides a chip holder comprising a chip-accommodating saucer for accommodating an inspection chip therein, a holder for holding the chip-accommodating saucer at a central portion of the holder, and a chip-pressing material for pressing the inspection chip accommodated in the chip-accommodating saucer against the chip-accommodating saucer, wherein a recess is provided in a central portion of the chip-accommodating saucer.

Effect of the Invention

According to the present invention, by heating and cooling the inspection chip by the thermocycling section disposed on one side of the holder-accommodating space, polymerase chain reaction can be carried out. Further, it is possible to take a picture of the inspection chip by the detector disposed on other side of the holder-accommodating space, it is possible to allow the inspection chip which carries out the polymerase chain reaction to inspect by the picture-taking operation, and it is possible to realize the real-time inspection.

BRIEF DESCRIPTION OF THE DRAWINGS

FIG. 5(a) is a perspective view showing the thermocycling section of the thermocycling inspection device and FIG. 5(b) is a perspective view showing a state where a chip holder is placed on the thermocycling section;

FIG. 8(a) is a plan view showing an exterior appearance of an inspection chip according to the embodiment of the invention, FIG. 8(b) is a side view of the inspection chip and FIG. 8(c) is an enlarged explanatory diagram showing a portion of a sample flow passage of the inspection chip;

EXPLANATION OF SYMBOLS

Figure 1:
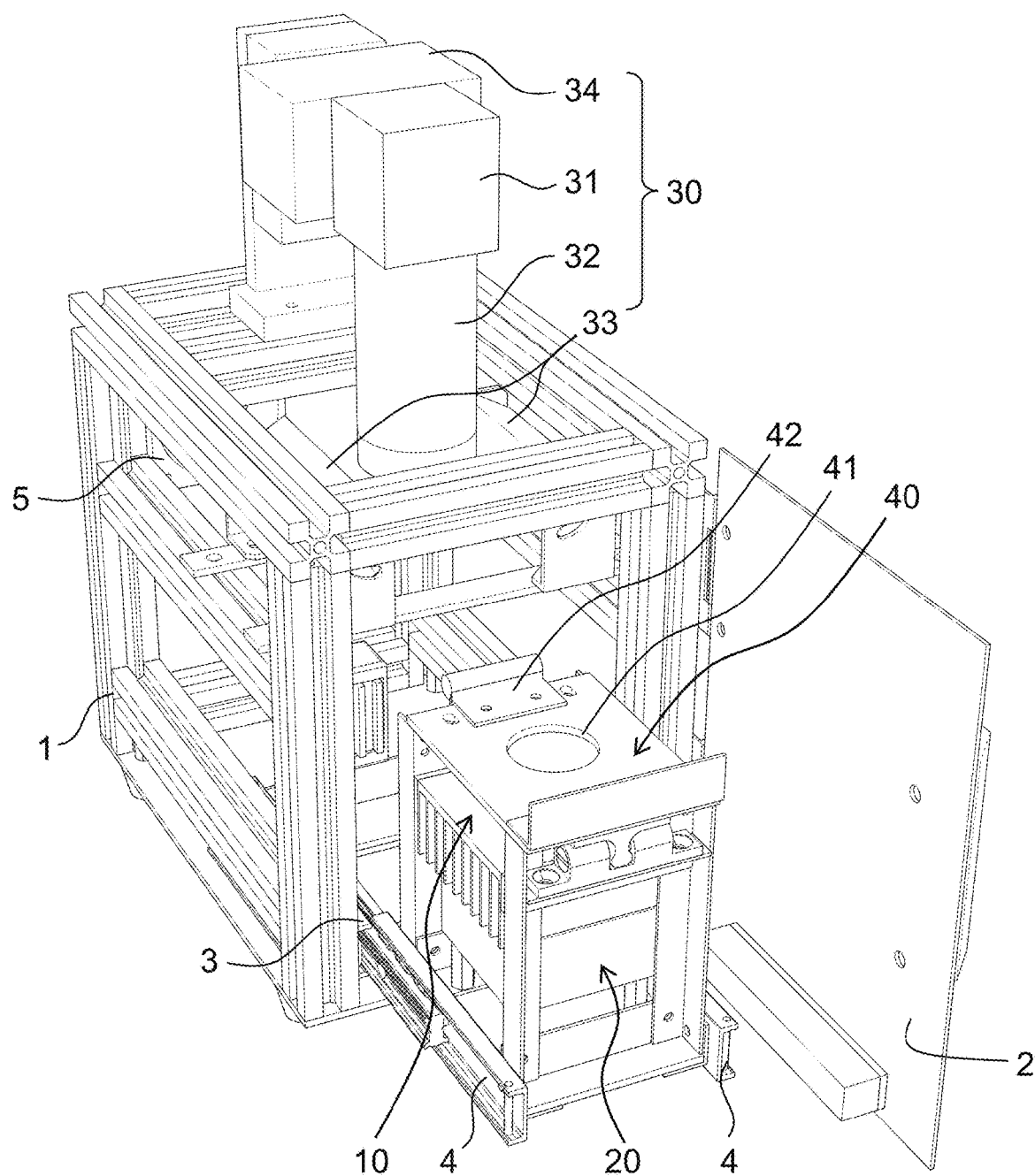
FIG. 1 is a perspective view showing an essential configuration of a thermocycling inspection device according to one of embodiments of the present invention.

10 holder-accommodating space
20 thermocycling section
21 Peltier element
21a one surface
21b other surface
22 heat sink
23 surface heater
24 cover plate
24a opening
25 temperature sensor
30 detector
40 holder-pressing lid
41 fluorescence detection window
43 transparent substrate
50 chip holder
51 chip-accommodating saucer
51a placing surface
51b wall surface
51c positioning projection
51d recess
52 holder
53 chip-pressing material
54 transparent film
60 inspection chip
61 positioning recess
62 sample introducing port
63 sample flow passage
C reagent
D sample solution
E oil (mineral oil)

MODE FOR CARRYING OUT THE INVENTION

According to the thermocycling inspection device of the first aspect of the invention, when the thermocycling section heats or cools or when a picture is taken by the detector, the thermocycling section is disposed on one side of the holder-accommodating space, the detector is disposed on other side of the holder-accommodating space, and the holder-accommodating space is formed such that an optical axis of the detector and the sample introducing port match with each other. According to this aspect, by heating and cooling the inspection chip by the thermocycling section disposed on one side of the holder-accommodating space, polymerase chain reaction can be carried out, it is possible to take a picture of the inspection chip by the detector disposed on other side of the holder-accommodating space, the inspection chip which carries out the polymerase chain reaction to inspect by the picture-taking operation, and POCT can be realized by the small device.

According to the second aspect of the invention, in the thermocycling inspection device of the first aspect, the thermocycling section includes a Peltier element, a heat sink disposed on one of surfaces of the Peltier element, a surface heater disposed on other surface of the Peltier element, and a cover plate which covers the surface heater and the other surface of the Peltier element, the holder-accommodating space is formed such that it covers the cover plate, an opening capable of abutting a chip-accommodating saucer of the chip holder against the surface heater is formed in the cover plate, and the inspection chip accommodated in the chip-accommodating saucer is heated by the surface heater. According to this aspect, it is possible to control the Peltier element into stable temperature by the heat sink disposed on the one surface of the Peltier element, and the inspection chip can be heated by the surface heater. Since the Peltier element can cool the surface heater by placing the surface heater on the other surface of the Peltier element, short cyclic temperature variation can be realized, and the polymerase chain reaction can stably be carried out.

According to the third aspect of the invention, in the thermocycling inspection device of the second aspect, a temperature sensor is disposed between the surface heater and the chip-accommodating saucer. According to this aspect, it is possible to more precisely detect the temperature of the inspection chip, and to stably carry out the polymerase chain reaction.

According to the fourth aspect of the invention, in the thermocycling inspection device of the second aspect, the thermocycling inspection device further comprises a holder-pressing lid which covers the chip holder disposed in the holder-accommodating space, a fluorescence detection window is formed in the holder-pressing lid, a transparent substrate is provided on the holder-pressing lid on a side of the holder-accommodating space, and the transparent substrate covers the fluorescence detection window and presses the chip holder. According to this aspect, adhesion between the chip-accommodating saucer and the surface heater is enhanced by pressing the chip holder by the transparent substrate and thus, heat of the surface heater can easily be transferred to the chip-accommodating saucer and thermal responsiveness of the chip-accommodating saucer can be enhanced.

According to the fifth aspect of the invention, in the thermocycling inspection device of the first aspect, the thermocycling section includes a Peltier element, a surface heater, a temperature sensor for detecting temperature of the inspection chip, and a control section for controlling temperature of the Peltier element and the surface heater, the surface heater heats the inspection chip, the Peltier element cools the surface heater, and the control section controls the surface heater and the Peltier element such that detection temperature detected by the temperature sensor is cyclically repeated between first set temperature and second set temperature which is lower than the first set temperature. According to this aspect, by heating the inspection chip by the surface heater and by cooling the surface heater by the Peltier element, the first set temperature can especially swiftly be shifted to the second set temperature, and the polymerase chain reaction can be carried out in a short time.

According to the sixth aspect of the invention, in the thermocycling inspection device of the fifth aspect, when the detection temperature detected by the temperature sensor detects the first set temperature, the control section turns the surface heater OFF and turns the Peltier element ON. According to this aspect, by not only turning the surface heater OFF but also forcibly cooling by the Peltier element, the first set temperature can swiftly be shifted to the second set temperature.

According to the seventh aspect of the invention, in the thermocycling inspection device of the fifth aspect, when the detection temperature detected by the temperature sensor detects the second set temperature, the control section feedback controls the surface heater such that the detection temperature becomes equal to the second set temperature in a state where the Peltier element is OFF, thereby maintaining the second set temperature for predetermined time. According to this aspect, by feedback controlling the surface heater in the OFF state of the Peltier element, it is possible to make the hunting small and to perform stable control.

The chip holder used for the thermocycling inspection device of the eighth aspect of the invention is used for the thermocycling inspection device of the first aspect, and comprises a chip-accommodating saucer for accommodating the inspection chip therein, a holder for holding the chip-accommodating saucer at a central portion of the holder, and a chip-pressing material for pressing the inspection chip accommodated in the chip-accommodating saucer against the chip-accommodating saucer, and the chip-pressing material is positioned by the holder. According to this aspect, by pressing the inspection chip against the chip-accommodating saucer by the chip-pressing material, adhesion between the inspection chip and the chip-accommodating saucer is enhanced and thus, heat of the chip-accommodating saucer can easily be transferred to the inspection chip, and thermal responsiveness of the inspection chip can be enhanced. According to this aspect, by holding the chip-accommodating saucer and by positioning the chip-pressing material by the holder, the inspection chip can reliably be pressed against the chip-accommodating saucer by the chip-pressing material, and it is possible to prevent the inspection chip from being damaged.

According to a chip holder of the ninth aspect, the chip holder includes a chip-accommodating saucer for accommodating the inspection chip therein, a holder for holding the chip-accommodating saucer at a central portion of the holder, and a chip-pressing material for pressing the inspection chip accommodated in the chip-accommodating saucer against the chip-accommodating saucer, and the chip-pressing material is positioned by the holder. According to this aspect, by pressing the inspection chip against the chip-accommodating saucer by the chip-pressing material, adhesion between the inspection chip and the chip-accommodating saucer is enhanced and thus, heat of the chip-accommodating saucer can easily be transferred to the inspection chip, and thermal responsiveness of the inspection chip can be enhanced. According to this aspect, by holding the chip-accommodating saucer and by positioning the chip-pressing material by the holder, the inspection chip can reliably be pressed against the chip-accommodating saucer by the chip-pressing material, and it is possible to prevent the inspection chip from being damaged.

According to the tenth aspect of the invention, in the chip holder of the ninth aspect, a positioning projection is formed on the chip-accommodating saucer, and a positioning recess corresponding to the positioning projection is formed in the inspection chip. According to this aspect, the inspection chip can precisely be positioned on the chip-accommodating saucer by the positioning projection and the positioning recess, the inspection chip can stably be heated and cooled and it is possible to precisely take a picture.

According to the eleventh aspect of the invention, in the chip holder of the ninth aspect, the chip-accommodating saucer is made of material having higher thermal conductivity than the holder. According to this aspect, by using the material having high thermal conductivity for the chip-accommodating saucer, the inspection chip can swiftly be heated and cooled. If material having low thermal conductivity is used for the holder, it is possible to prevent heat from being dispersed toward the holder, and to enhance the thermal conductivity of the inspection chip.

According to the twelfth aspect of the invention, in the chip holder of the ninth aspect, a recess is provided in a central portion of the chip-accommodating saucer. According to this aspect, it is possible to prevent the specimen liquid charged from the sample introducing port from flowing out toward the chip-accommodating saucer.

According to the thirteenth aspect of the invention, in the chip holder of the ninth aspect, the chip holder further includes a transparent film which is attached to the holder to prevent oil added to the chip-accommodating saucer from overflowing. According to this aspect, by attaching the transparent film to the holder, it is possible to prevent oil supplied to the chip-accommodating saucer from leaking out, and the chip holder can easily be handled.

In a thermocycling inspection device of the fourteenth aspect of the invention, a thermocycling section includes a Peltier element, a heat sink disposed on one of surfaces of the Peltier element, a surface heater disposed on other surface of the Peltier element, and a cover plate which covers the surface heater and the other surface of the Peltier element, the holder-accommodating space is formed to cover the cover plate, an opening is formed in the cover plate, and a fluorescence detection window for taking a picture of the inspection chip by the detector is formed in the holder-pressing lid. According to this aspect, it is possible to control the Peltier element into stable temperature by the heat sink disposed on the one surface of the Peltier element, and the inspection chip can be heated by the surface heater. Since the Peltier element can cool the surface heater by placing the surface heater on the other surface of the Peltier element, short cyclic temperature variation can be realized, and the polymerase chain reaction can stably be carried out.

A chip holder of the fifteenth aspect of the invention comprises a chip-accommodating saucer for accommodating an inspection chip therein, a holder for holding the chip-accommodating saucer at a central portion of the holder, and a chip-pressing material for pressing the inspection chip accommodated in the chip-accommodating saucer against the chip-accommodating saucer, and a recess is provided in a central portion of the chip-accommodating saucer. According to this aspect, by pressing the inspection chip against the chip-accommodating saucer by the chip-pressing material, adhesion between the inspection chip and the chip-accommodating saucer is enhanced and thus, heat of the chip-accommodating saucer can easily be transferred to the inspection chip, and thermal responsiveness of the inspection chip can be enhanced. Further, according to this aspect, it is possible to prevent the specimen liquid charged from the sample introducing port from flowing out toward the chip-accommodating saucer.

EMBODIMENTS

One of embodiments of a thermocycling inspection device of the present invention will be described below.

Figure 2:
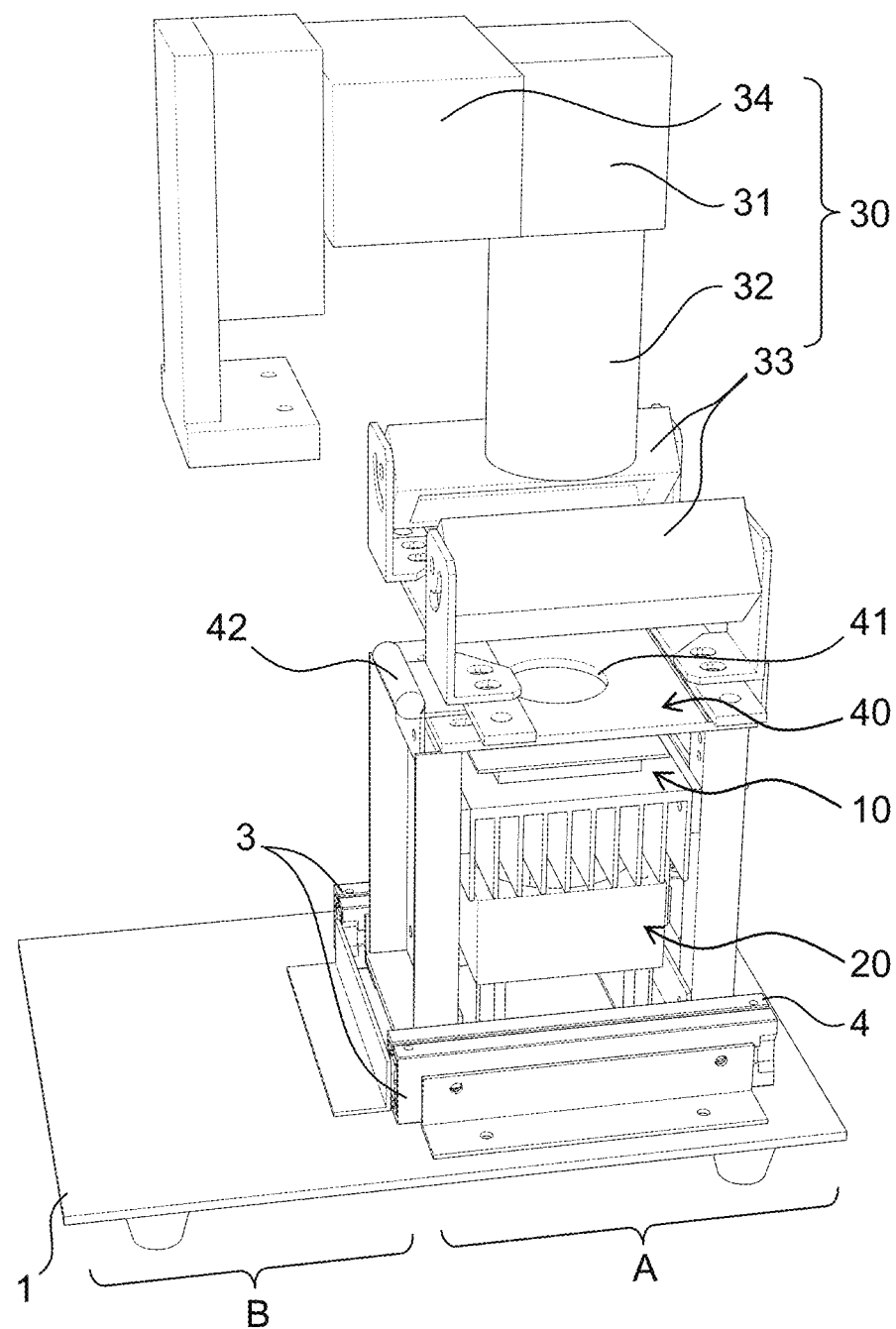
FIG. 2 is a perspective view showing an essential portion of the thermocycling inspection device.
Figure 3:
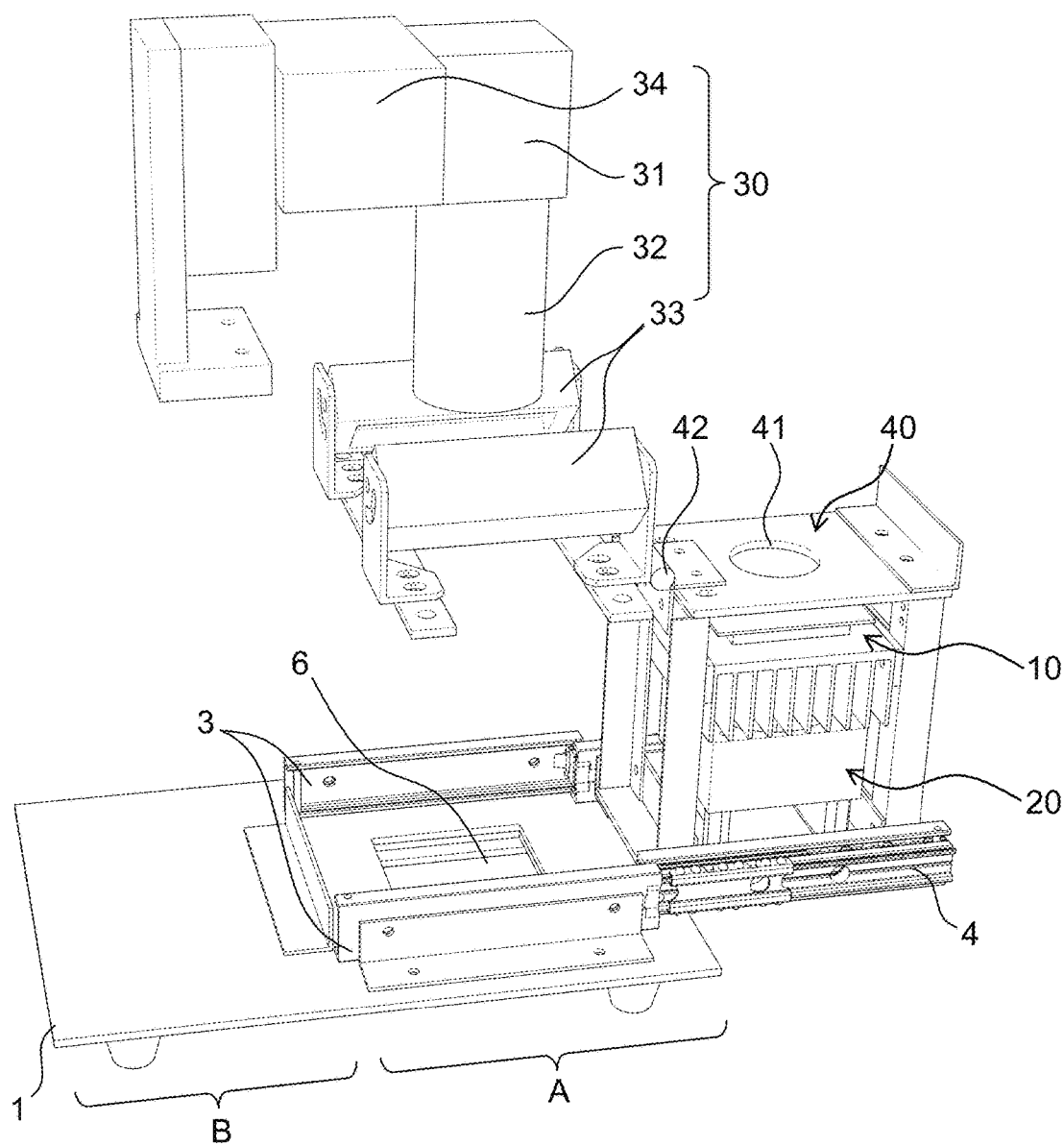
FIG. 3 is a perspective view showing a state where a portion of the essential portion of the thermocycling inspection device shown in FIG. 2 is moved.

FIG. 1 is a perspective view showing an essential configuration of the thermocycling inspection device according to the embodiment, FIG. 2 is a perspective view showing an essential portion of the thermocycling inspection device and FIG. 3 is a perspective view showing a state where a portion of the essential portion of the thermocycling inspection device shown in FIG. 2 is moved.

The thermocycling inspection device of the embodiment includes holder-accommodating space 10 for accommodating a chip holder, a thermocycling section 20 for heating and cooling an inspection chip, and a detector 30 for taking a picture of the inspection chip.

The holder-accommodating space 10 is formed above the thermocycling section 20. A holder-pressing lid 40 is provided above the holder-accommodating space 10 which covers a chip holder. The chip holder is disposed in the holder-accommodating space 10.

The casing 1 is provided at its front surface with a front door 2, and at its interior both side surfaces or interior bottom surface with a pair of guiders 3. The pair of guiders 3 slide on a pair of slide rails 4.

The holder-accommodating space 10, the thermocycling section 20 and the holder-pressing lid 40 can be pulled out forward from the front surface of the casing 1 by the pair of slide rails 4.

FIGS. 1 and 3 show a state where the holder-accommodating space 10, the thermocycling section 20 and the holder-pressing lid 40 are pulled out outward from the casing 1, and FIG. 2 shows a state where the holder-accommodating space 10, the thermocycling section 20 and the holder-pressing lid 40 are accommodated in the casing 1.

As shown in FIGS. 2 and 3, an interior of the casing 1 is divided into a front space A and a rear space B. The holder-accommodating space 10, the thermocycling section 20 and the holder-pressing lid 40 are accommodated in the front space A. A control section is accommodated in the rear space B. The control section controls a Peltier element and a surface heater based on detection temperature detected by a temperature sensor.

A fluorescence detection window 41 is formed in the holder-pressing lid 40. The holder-pressing lid 40 is provided with a torque hinge 42.

As shown in FIG. 1, the rear space B is provided with a cooling fan 5 for discharging air in the casing 1.

As shown in FIG. 3, in the front space A, an intake port 6 is formed in a bottom surface of the casing 1.

Air which is sucked from the intake port 6 into the casing 1 by driving the cooling fan 5 is discharged out from an exhaust port formed in the front space A.

A detector 30 is disposed above the casing 1. The detector 30 is composed of a camera 31, a camera lens 32, a pair of lighting LEDs 33 and a holding material 34.

The camera 31 is held above the casing 1 by the holding material 34. A lower portion of the camera 31 holds the camera lens 32.

The pair of lighting LEDs 33 are disposed on both sides of the camera lens 32 and are mounted on upper portions in the front space A.

An optical axis of the camera lens 32 coincides with a center of the fluorescence detection window 41, and optical axes of the pair of lighting LEDs 33 are directed toward the fluorescence detection window 41.

As shown in FIG. 2, in a state where the holder-accommodating space 10, the thermocycling section 20 and the holder-pressing lid 40 are accommodated in the casing 1, i.e., when the thermocycling section 20 heats or cools and the detector 30 takes a picture, the thermocycling section 20 is disposed on one side of the holder-accommodating space 10 and the detector 30 is disposed on other side of the holder-accommodating space 10.

The holder-accommodating space 10 is formed such that the optical axis of the detector 30 coincides with a sample introducing port formed in a central portion of the inspection chip.

According to this embodiment, if the thermocycling section 20 which is disposed on one side of the holder-accommodating space 10 heats and cools, polymerase chain reaction can be carried out, the detector 30 disposed on the other side of the holder-accommodating space 10 can take a picture of the inspection chip, the inspection chip which carried out the polymerase chain reaction can be inspected by the picture-taking operation, and a POCT (real time inspection) can be realized with a small-sized device.

Figure 4A:
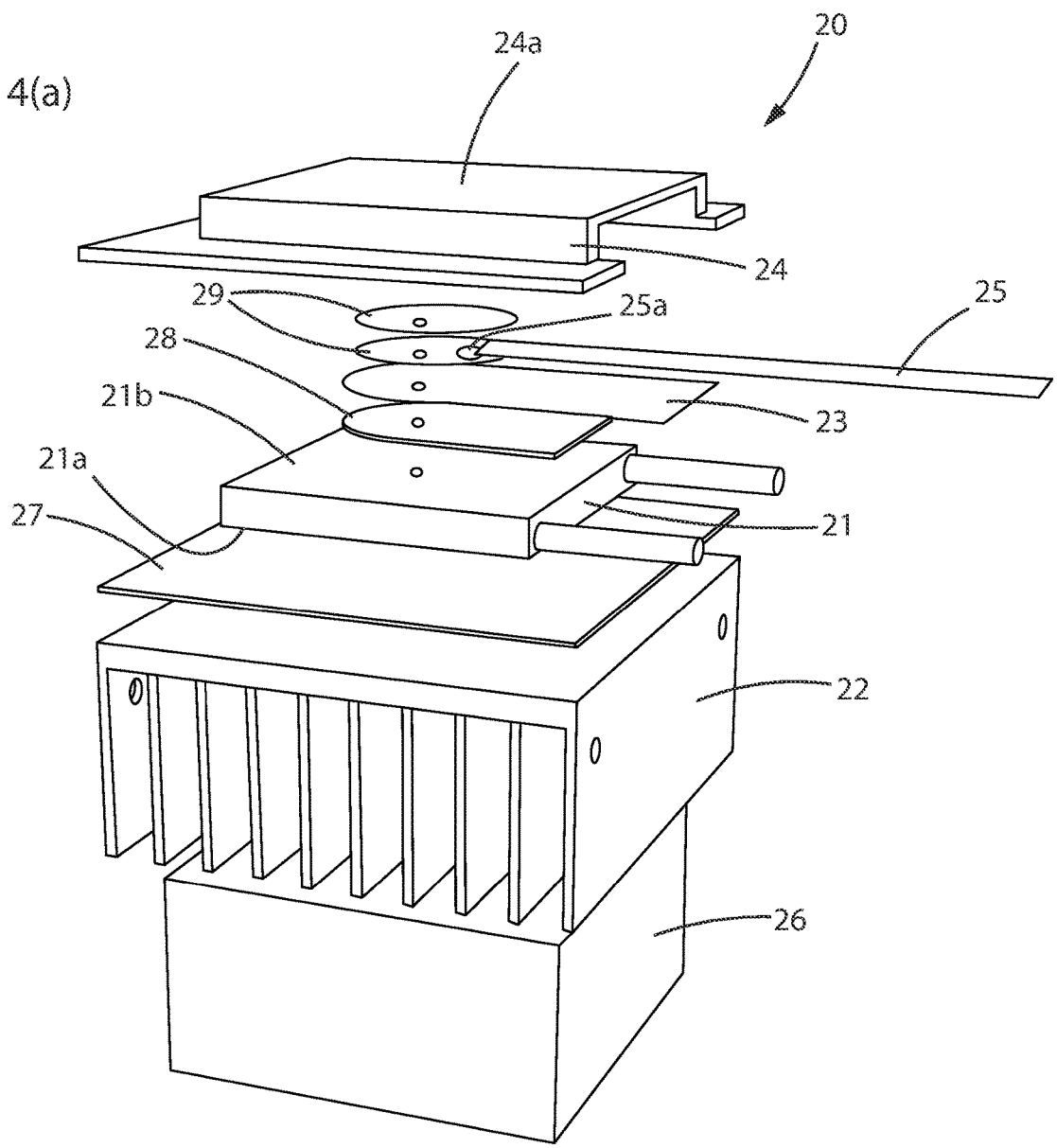
FIG. 4(a) is an exploded perspective view showing a thermocycling section of the thermocycling inspection device and FIG. 4(b) shows a configuration of a temperature sensor.
Figure 4B:
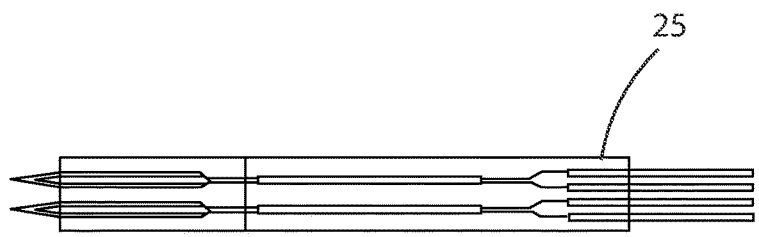

FIG. 4(a) is an exploded perspective view showing the thermocycling section of the thermocycling inspection device and FIG. 4(b) shows a configuration of the temperature sensor.

The thermocycling section 20 includes a Peltier element 21, a heat sink 22 disposed on one surface 21a of the Peltier element 21, a surface heater 23 disposed on the other surface 21b of the Peltier element 21, a cover plate 24 which covers the surface heater 23 and the other surface 21b of the Peltier element 21, a temperature sensor 25 for detecting temperature of the Peltier element, and a fan 26 for enhancing heat exchanging performance of the heat sink 22.

The one surface 21a of the Peltier element 21 is adhered to the heat sink 22 by a thermal conductivity adhesive transfer tape 27. The surface heater 23 is adhered to the other surface 21b of the Peltier element 21 by a thermal conductivity adhesive transfer tape 28. An opening 24a is formed in a central portion of the cover plate 24. The temperature sensor 25 is disposed on a surface of the surface heater 23 on the side of the cover plate 24. A detecting section 25a of the temperature sensor 25 is sandwiched between two thermal diffusion sheets 29. The thermal diffusion sheets 29 are disposed at positions opposed to the opening 24a of the cover plate 24. It is preferable that the thermal diffusion sheets 29 have the same sizes as the inspection chip, and the size of the thermal diffusion sheets 29 are equal to or larger than an outer diameter of the inspection chip and equal or smaller than the opening 24a.

A recess is formed in the other surface 21b of the Peltier element 21. Holes are formed in the thermal conductivity adhesive transfer tape 28, the surface heater 23 and the two thermal diffusion sheets 29. The recess of the Peltier element 21, the hole of the thermal conductivity adhesive transfer tape 28, the hole of the surface heater 23 and the holes of the two thermal diffusion sheets 29 can be utilized as positioning operations using pins at the time of assembling operation.

The fan 26 is disposed such that it is opposed to a fin surface of the heat sink 22.

According to this embodiment, by using the surface heater 23, it is possible to reduce heat accumulation by heating, and realize the short-time temperature variation.

The temperature sensor 25 is not limited to a sensor which directly detects the temperature of the inspection chip, and the temperature sensor 25 may detect the temperature of the surface heater 23 and may indirectly detect the temperature of the inspection chip as in this embodiment.

It is preferable that the temperature sensor 25 includes two thermocouples as shown in FIG. 4(b). If the temperature sensor 25 is composed of the plurality of thermocouples and is provided with a plurality of circuits which are arranged in parallel in this manner, it is possible to prevent the control section from running away.

FIG. 5(a) is a perspective view showing the thermocycling section of the thermocycling inspection device and FIG. 5(b) is a perspective view showing a state where the chip holder is placed on the thermocycling section.

As shown in FIG. 5(a), the cover plate 24 covers the surface heater 23 and the Peltier element 21. The holder-accommodating space 10 is formed above and around the cover plate 24 to cover the cover plate 24.

As shown in FIG. 5(b), the chip holder 50 is disposed in the holder-accommodating space 10.

Figure 6A:
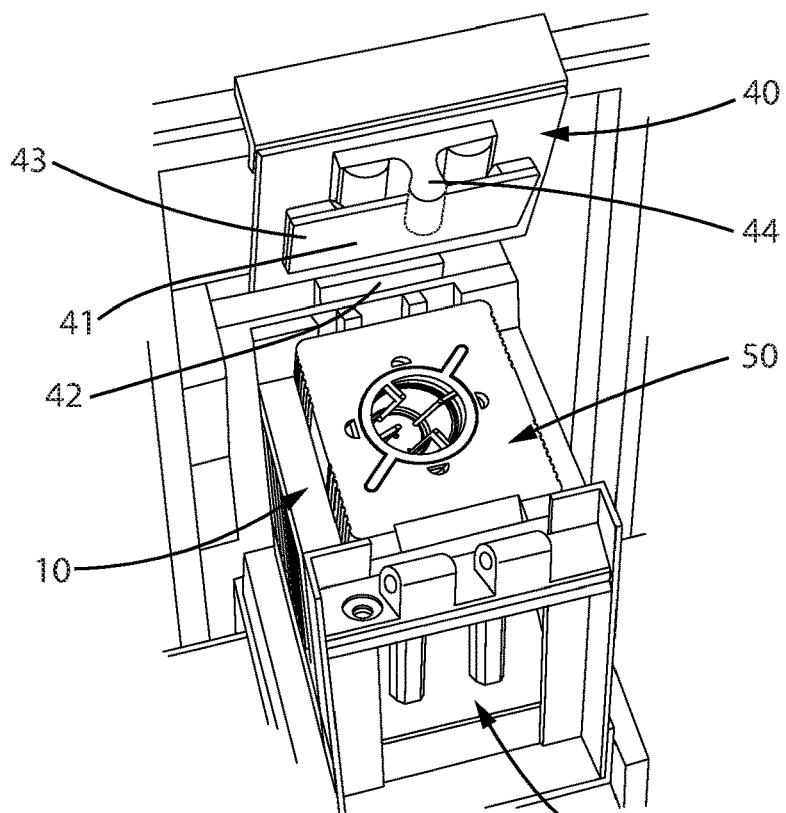
FIG. 6(a) is a photograph showing an attached state of the chip holder to the thermocycling inspection device and FIG. 6(b) is an enlarged perspective view of an essential portion of the ed state of the chip holder to the thermocycling inspection device.
Figure 6B:
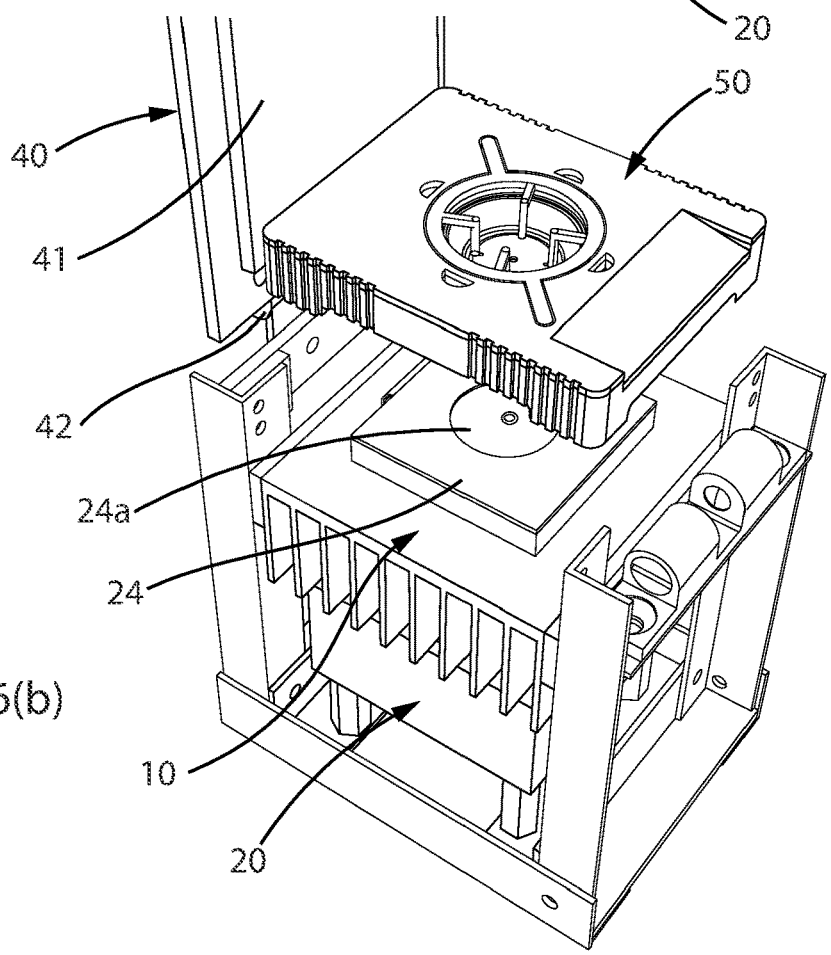

FIG. 6(a) is a photograph showing an attached state of the chip holder to the thermocycling inspection device and FIG. 6(b) is an enlarged perspective view of an essential portion of the attached state of the chip holder to the thermocycling inspection device.

FIG. 6 show a state where the holder-pressing lid 40 is opened.

The holder-pressing lid 40 is provided with a transparent substrate 43 and a lock member 44 on the side of the holder-accommodating space 10.

The transparent substrate 43 covers the fluorescence detection window 41 and presses the chip holder 50 in a state where he holder-pressing lid 40 is closed. In the state where the holder-pressing lid 40 is closed, a state where the holder-pressing lid 40 is closed by the lock member 44 is maintained.

FIG. 7(a) is an exploded perspective view of the chip holder used in the thermocycling inspection device, FIG. 7(b) is a perspective view of the chip holder and FIG. 7(c) is a side sectional view of the chip holder.

The chip holder 50 of this embodiment includes a chip-accommodating saucer 51 for accommodating the inspection chip 60 therein, a holder 52 for holding the chip-accommodating saucer 51 by its central portion, and a chip-pressing material 53 which presses, against the chip-accommodating saucer 51, the inspection chip 60 accommodated in the chip-accommodating saucer 51.

The chip-accommodating saucer 51 is formed by a placing surface 51a on which the inspection chip 60 is placed, and a wall surface Kb which covers an outer periphery of the placing surface 51a. The wall surface 51b is formed into a mortar shape such that a width thereof becomes wider upward. The chip-accommodating saucer 51 is formed into a recessed-shape by the placing surface 51a and the wall surface 51b.

A ring-shaped recess 52b, positioning recesses 52c and fixing holes 52d are formed in an upper surface 52a of the holder 52. The ring-shaped recesses 52b are formed around an outer periphery of the chip-accommodating saucer 51, the positioning recesses 52c are continuous with the ring-shaped recess 52b, and the fixing holes 52d are formed in portions of the positioning recesses 52c.

The chip-pressing material 53 is formed by a ring portion 53a, positioning legs 53b, fixing projections 53c and chip pressing legs 53d. The ring portion 53a is mounted on the ring-shaped recess 52b, the positioning legs 53b are mounted on the positioning recesses 52c, and the fixing projections 53c are mounted to the fixing holes 52d.

If the ring portion 53a is mounted on the ring-shaped recess 52b and the positioning legs 53b are mounted on the positioning recesses 52c, the chip-pressing material 53 is positioned on the holder 52. If the fixing projections 53c are fitted into the fixing holes 52d, the chip-pressing material 53 is fixed to the holder 52.

Each of the chip pressing legs 53d is composed of a horizontal member 53d1 which horizontally extends inward from the ring portion 53a, and a vertical member 53d2 which vertically extends from a tip end of the horizontal member 53d1 toward the placing surface 51a. An upper surface of a tip end of the horizontal member 53d1 is provided with a projection 53d3 which projects upward.

In a state where the chip-pressing material 53 is fixed to the holder 52, an upper surface of the chip-pressing material 53 excluding the projections 53d3 and the upper surface 52a of the holder 52 form the same plane. Therefore, if the transparent substrate 43 shown in FIG. 7(c) is abutted against the upper surface 52a of the holder 52, the transparent substrate 43 presses the projections 53d3.

Tip ends of the horizontal members 53d1 can be bent by elasticity of the horizontal members 53d1. If the transparent substrate 43 presses the projections 53d3, the vertical members 53d2 press the inspection chip 60 against the placing surface 51a of the chip-accommodating saucer 51.

According to this embodiment, if the transparent substrate 43 presses the chip holder 50, adhesion between the chip-accommodating saucer 51 and the surface heater 23 is enhanced and hence, heat of the surface heater 23 can easily be transferred to the chip-accommodating saucer 51, and thermal responsiveness of the chip-accommodating saucer 51 can be enhanced.

Further, according to the embodiment, if the chip-pressing material 53 presses the inspection chip 60 against the chip-accommodating saucer 51, adhesion between the inspection chip 60 and the chip-accommodating saucer 51 is enhanced and hence, heat of the chip-accommodating saucer 51 can easily be transferred to the inspection chip 60 and the thermal responsiveness of the inspection chip 60 can be enhanced.

In this embodiment, if the chip-accommodating saucer 51 is held by the holder 52 and the chip-pressing material 53 is positioned, the inspection chip 60 can reliably be pressed against the chip-accommodating saucer 51 by the chip-pressing material 53, and it is possible to prevent the inspection chip 60 from being damaged.

The positioning projections 51c are formed on the placing surface 51a of the chip-accommodating saucer 51 and the positioning recesses 61 corresponding to the positioning projections 51c are formed in the inspection chip 60.

According to this embodiment, the inspection chip 60 can precisely be positioned on the chip-accommodating saucer 51 by the positioning projections 51c and the positioning recesses 61, the inspection chip 60 can stably be heated and cooled, and it is possible to precisely take a picture.

The chip-accommodating saucer 51 is made of material having higher thermal conductivity than the holder 52. For example, when the holder 52 is made of resin, the chip-accommodating saucer 51 should be made of metal material such as aluminum, iron and copper, or should be made of thermal conductivity resin, or ceramic having high thermal conductivity such as aluminum nitride having higher thermal conductivity than resin of the holder 52. It is preferable that only the placing surface 51a instead of the entire chip-accommodating saucer 51, or only a portion of the placing surface 51a on which the inspection chip 60 is placed is made of material having higher thermal conductivity than the holder 52.

According to this embodiment, if the chip-accommodating saucer 51 or the placing surface 51a is made of material having high thermal conductivity, it is possible to swiftly heat and cool the inspection chip 60, and if the holder 52 is made of material having low thermal conductivity on the other hand, it is possible to prevent heat from diffusing toward the holder 52, and thermal conductivity of the inspection chip 60 can be enhanced.

A sample introducing port 62 is formed in a central portion of the inspection chip 60. A recess 51d is formed in a central portion of the chip-accommodating saucer 51. A projection projecting toward the thermocycling section 20 is formed on a central portion of the recess 51d. This projection is formed by a nozzle portion when the chip-accommodating saucer 51 is formed by injection molding. This projection is disposed in the recess of the Peltier element 21, the hole of the thermal conductivity adhesive transfer tape 28, the hole of the surface heater 23 and the holes of the two thermal diffusion sheets 29 when the chip holder 50 is attached to the thermocycling section 20. Therefore, this projection is not pressed by the thermocycling section 20. That is, the inspection chip 60 is not pressed by the recess 51d and it is possible to prevent the inspection chip 60 from being damaged.

FIG. 8 show exterior appearance of the inspection chip of the one of the embodiments of the present invention, wherein FIG. 8(a) is a plan view, FIG. 8(b) is a side view and FIG. 8(c) is an enlarged explanatory diagram showing a portion of the sample flow passage.

The inspection chip 60 is formed by the sample introducing port 62 formed in a central portion thereof, and a plurality of sample flow passages 63 radially extending from the sample introducing port 62.

As shown in the side view of FIG. 8(b), the inspection chip 60 can be formed by bonding a first substrate 60a, a second substrate 60b and a third substrate 60c to one another.

The first substrate 60a includes the sample introducing port 62, the second substrate 60b includes the sample flow passages 63, and the third substrate 60c includes the sample discharge port 64. The first substrate 60a, the second substrate 60b and the third substrate 60c are made of glass or plastic. As the glass, it is possible to use silica glass, other glasses or synthetic resin. It is preferable that at least one of the first substrate 60a and the third substrate 60c is made of translucent material, and the translucent material is transparent.

The sample introducing port 62 is formed as a hole which passes through front and back sides of the first substrate 60a, the sample flow passages 63 are formed as holes which pass through front and back sides of the second substrate 60b and are formed as slits which radially extends from the holes, and the sample discharge port 64 is formed as a hole which passes through front and back sides of the third substrate 60c. This embodiment shows a case where the large number of sample flow passages 63 are formed by eight slits. The eight slits are disposed at equal intervals from one another in the radial direction around a hole formed in a central portion. It is preferable that a hole diameter of the sample discharge port 64 is the same as a hole diameter of the sample introducing port 62, and hole diameters of the sample discharge port 64 and the sample introducing port 62 are larger than a width of the slit, and are larger than a hole of the central portion of the second substrate 60b.

In the inspection chip 60 of this embodiment, the eight sample flow passages 63 are formed around the sample introducing port 62 and the sample discharge port 64.

The eight sample flow passages 63 have the same lengths and are disposed radially around the sample introducing port 62 and the sample discharge port 64, and outer peripheral ends of the sample flow passages 63 are opened.

As shown in FIG. 8(c), the sample flow passages 63 are formed as square hollow grooves by the first substrate 60a and the third substrate 60c, and each of the hollow grooves has four angles. By forming such four acute (not roundish) angles in this manner, it is possible to reliably fix a reagent C to the sample flow passages 63.

By making slit depths (plate thickness of second substrate 60b) of the sample flow passages 63 larger than the slit width, it is possible to reliably discriminate even if fluorescence reaction is weak.

Figure 9:
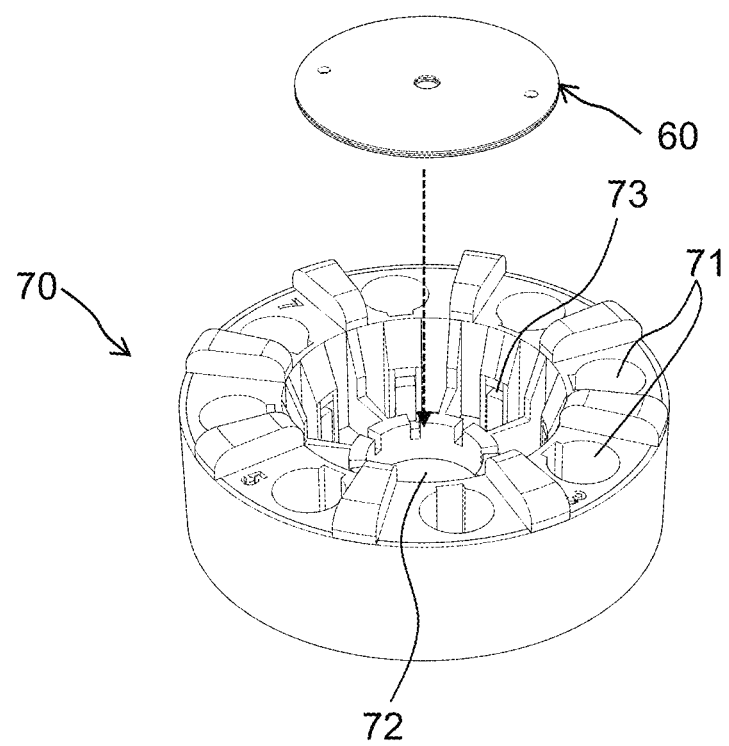
FIG. 9 is a perspective view of a reagent-rubbing device which is suitable for the inspection chip.

FIG. 9 is a perspective view of a reagent-rubbing device which is suitable for the inspection chip of the embodiment.

The reagent-rubbing device 70 is provided at its outer peripheral portion with a plurality of reagent pools 71. The reagent-rubbing device 70 is also provided at its inner peripheral portion with a space 72 on which the inspection chip 60 can be laminated. The reagent-rubbing device 70 is also provided at its inner peripheral surface with reagent supply ports 73 through which a reagent introduced from the reagent pools 71 is supplied.

Since the inspection chip 60 of the embodiment includes the eight sample flow passages 63, the number of the reagent pools 71 and the number of the reagent supply ports 73 are eight.

Reagents supplied from the reagent pools 71 pass through the respective reagent supply ports 73 and are introduced from the openings of the sample flow passages 63 by capillary action.

That is, if a reagent comes into contact with the opening of the sample flow passage 63, the reagent actively flows into the sample flow passage 63 by the capillary action, and the sample flow passage 63 is reliably filled with the reagent by surface tension which acts around ends of the sample flow passage 63 facing the sample introducing port 62 and the sample discharge port 64.

If the reagent is dried in a state where the sample flow passages 63 is filled with the reagent, the reagent is fixed in the square hollow groove. The reagent is fixed to the four angles of the square hollow groove, or fixed in a mesh shape in the square hollow groove.

In this embodiment, different reagents are introduced into and fixed to the respective sample flow passages 63. In this case, the reagents are introduced into the respective sample flow passages 63 in sequence, or different reagents are introduced into all of the sample flow passages 63 at the same time. After the reagents are introduced into all of the sample flow passages 63, the reagents are fixed by drying the reagents.

If the reagent is provided with appropriate viscosity using an appropriate matrix, unevenness of concentration of a reagent can be prevented in the sample flow passages 63. As the matrix, it is possible to use any one of polyethylene glycol, glycerol, polysaccharide, protein, surface-active agent and surface-active agent, or a mixture thereof.

Figure 7:
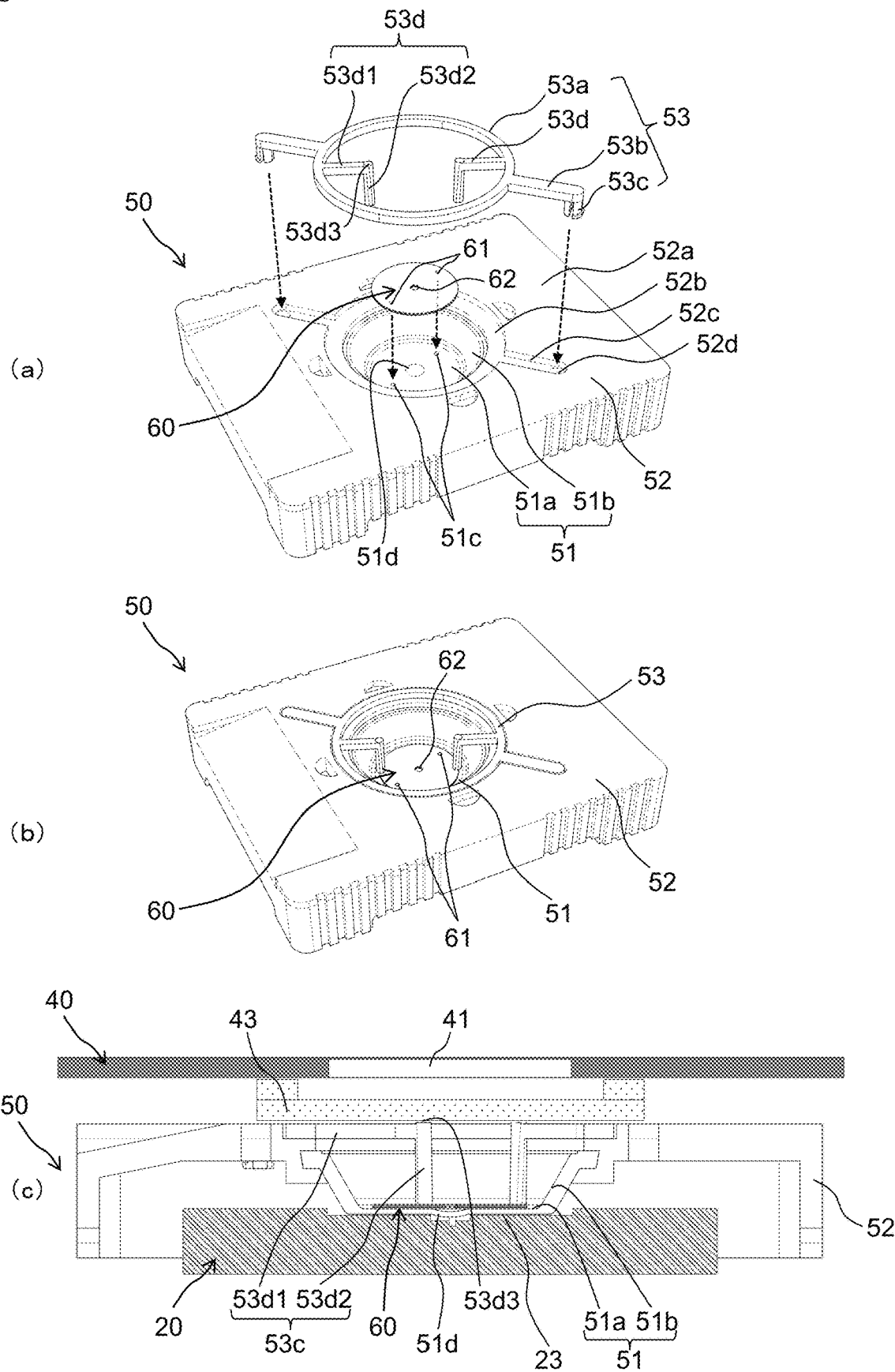
FIG. 7(a) is an exploded perspective view of the chip holder used in the thermocycling inspection device.
FIG. 7(b) is a perspective view of the chip holder and FIG. 7(c) is a side sectional view of the chip holder.

In the inspection chip 60 accommodated in the chip holder 50 shown in FIGS. 7, the reagent is fixed to the sample flow passage 63.

After specimen liquid (sample solution) which is to be measured as will be explained later is introduced into the inspection chip 60, the chip holder 50 shown in FIG. 7 is set in the thermocycling inspection device shown in FIGS. 1 to 3.

Figure 10:
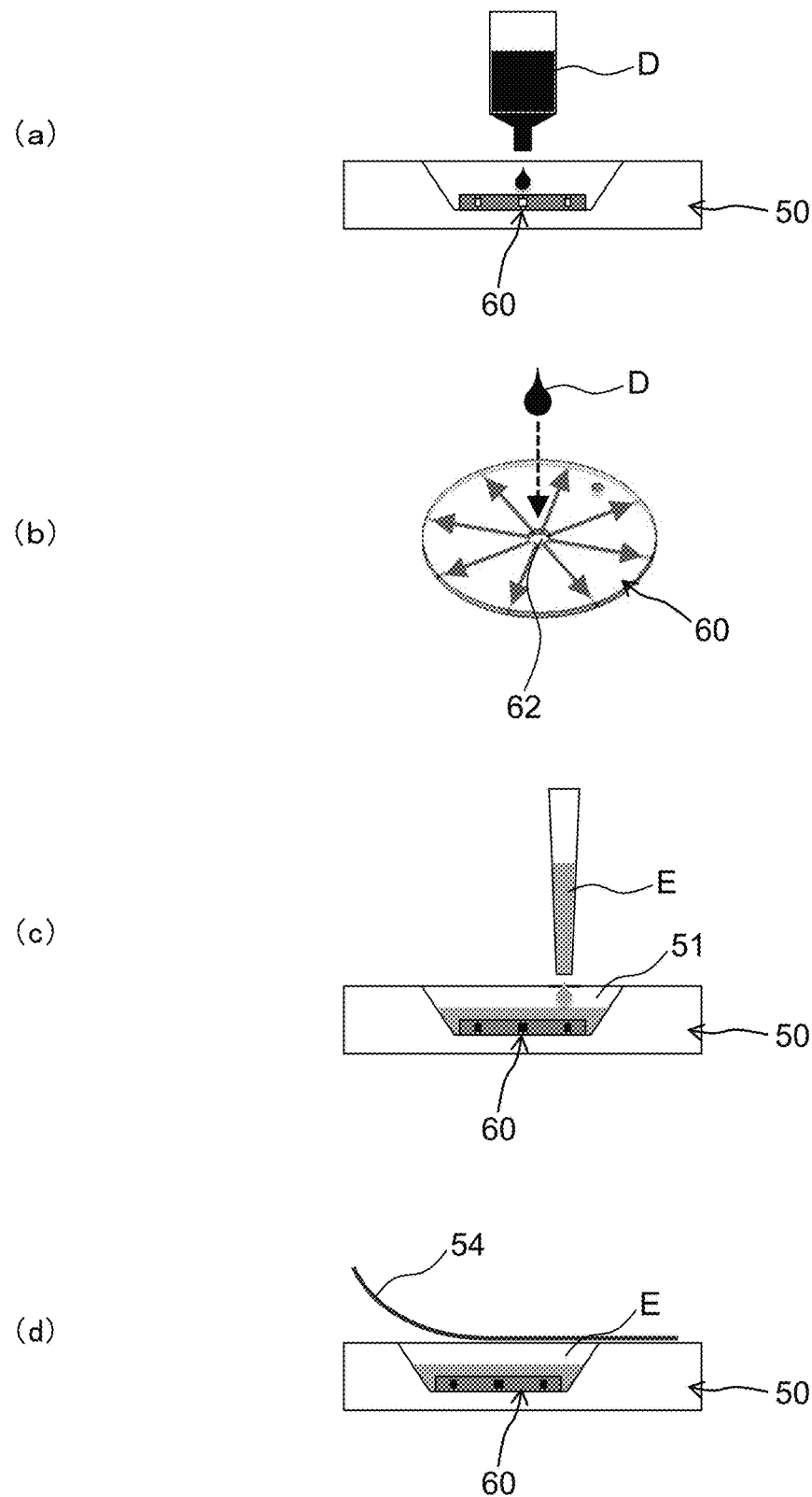
FIG. 10 are explanatory diagrams showing an introducing step of sample solution into the chip holder according to the embodiment.

FIG. 10 are explanatory diagrams showing an introducing step of sample solution into the chip holder according to the embodiment.

An extracted specimen is added to nucleic acid extraction liquid, nucleic acid is extracted by heating and ultrasonic fragmentation operations. A detected reagent is mixed into the extracted nucleic acid to form sample solution D.

FIG. 10(a) shows a dropping step of the sample solution D into the chip holder 50.

The sample solution is introduced from the sample introducing port 62 by the capillary action.

As shown in FIG. 10(b), if the sample solution D comes into contact with the sample introducing port 62, the sample solution D actively flows into the sample flow passage 63 by the capillary action, and the sample flow passages 63 is reliably filled with the sample solution D by surface tension which acts in the opening of the sample flow passage 63.

As explained in FIG. 7, since the recess 51d is formed in the central portion of the chip-accommodating saucer 51, it is possible to prevent the sample solution D charged from the sample introducing port 62 from flowing out into the chip-accommodating saucer 51.

A reagent C which is already fixed is melted into the sample solution D which is introduced into the sample flow passage 63, the sample solution D and the reagent C are mixed, and the temperature is managed into a more appropriate condition. According to this, reaction between the sample solution D and the reagent C is started.

FIG. 10(c) shows an introducing step of oil (mineral oil) E into the chip-accommodating saucer 51 for preventing evaporation and drying of the sample solution D. If oil is added, both ends of the flow passage formed in the inspection chip 60 can be closed with the mineral oil E. Solution in the flow passage which is oil-sealed in this manner does not evaporate, and the solution is not dried even if temperature variation is repeated.

As shown in FIG. 10(d), after the oil E is introduced into the chip-accommodating saucer 51, and a transparent film 54 is attached to the upper surface 52a of the holder 52, thereby preventing the oil E which is added to the chip-accommodating saucer 51 from overflowing.

According to this embodiment, by attaching the transparent film 54 to the holder 52, it is possible to prevent the oil E which is added to the chip-accommodating saucer 51 from leaking out, and the chip holder 50 can be handled easily.

Figure 11:
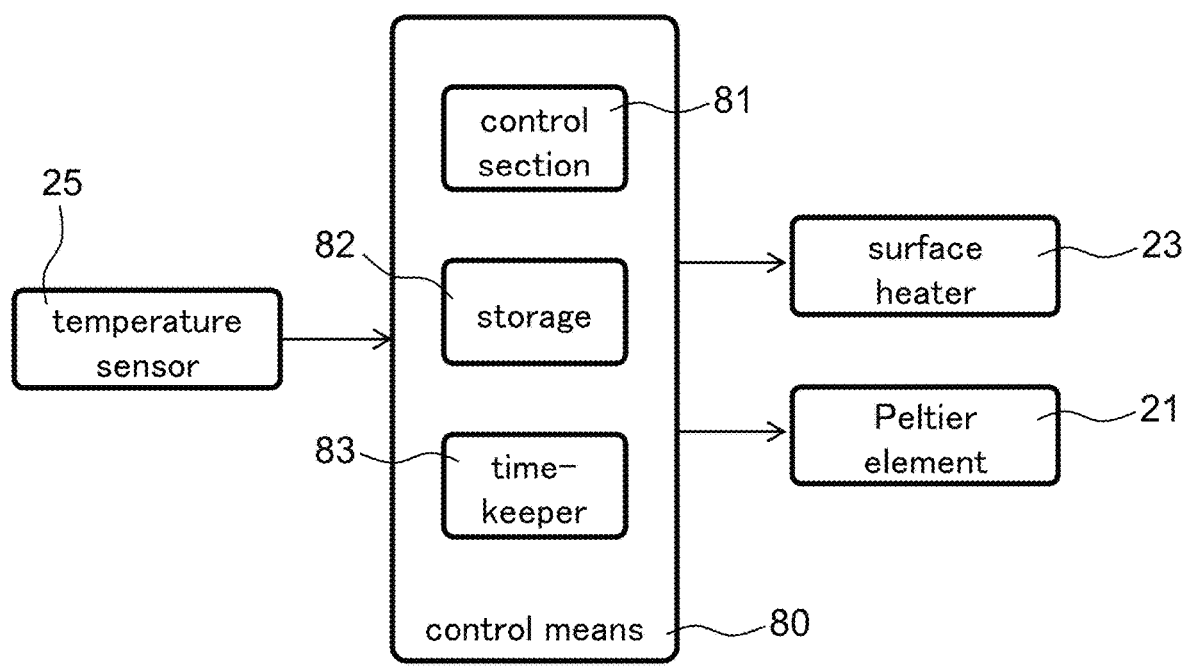
FIG. 11 is a block diagram for controlling the thermocycling inspection device according to the embodiment.
Figure 12:
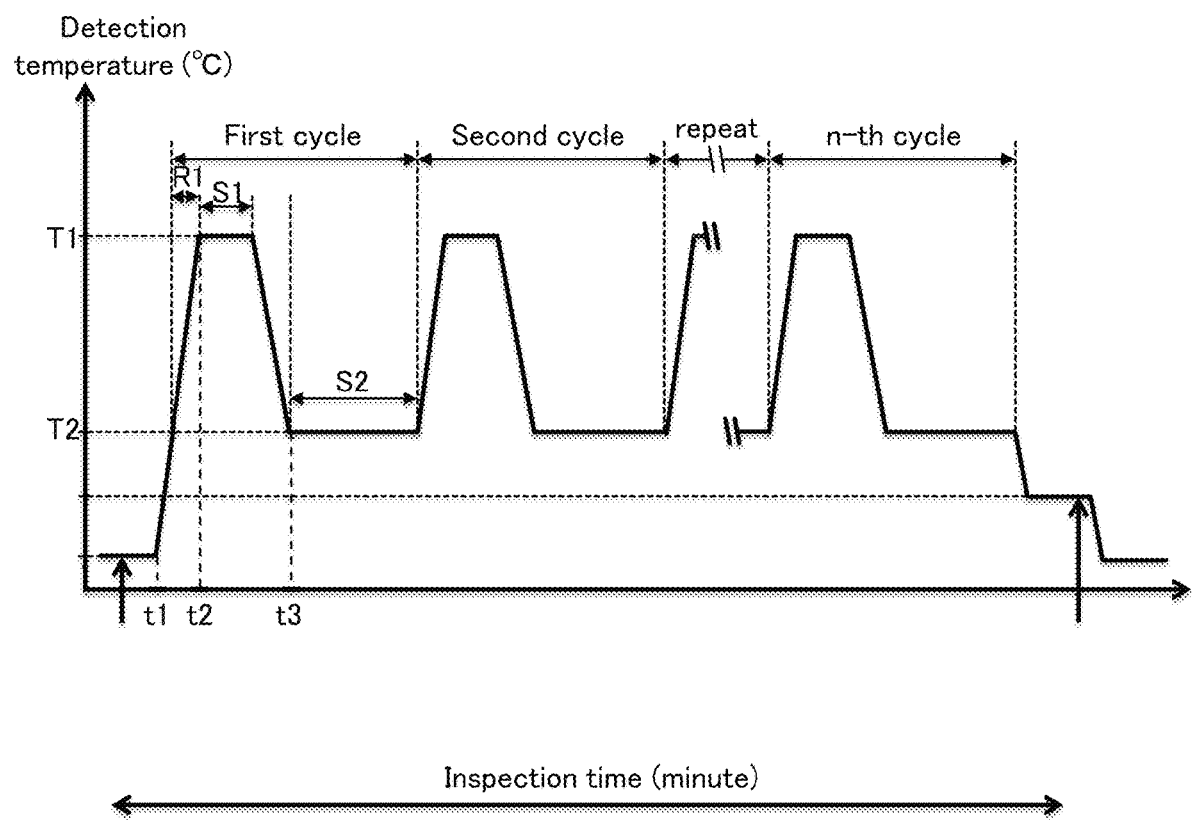
FIG. 12 is a graph showing temperature variation of the inspection chip.

FIG. 11 is a block diagram for controlling the thermocycling inspection device according to the embodiment and FIG. 12 is a graph showing temperature variation of the inspection chip.

The thermocycling section 20 includes the Peltier element 21, the surface heater 23, the temperature sensor 25 and control means 80.

The control means 80 includes a control section 81 for controlling temperature of the Peltier element 21 and the surface heater 23, a storage 82 for storing set temperature and set time, and a timekeeper 83 for keeping time.

The surface heater 23 heats the inspection chip 60, and the Peltier element 21 cools the surface heater 23.

The control section 81 controls the surface heater 23 and the Peltier element 21 such that detection temperature detected by the temperature sensor 25 is cyclically repeated between first set temperature T1 and second set temperature T2 which is lower than the first set temperature T1.

When the detection temperature detected by the temperature sensor 25 detects the first set temperature T1, the control section 81 turns the surface heater 23 OFF and turns the Peltier element 21 ON.

At time t1 in FIG. 12, the surface heater 23 is turned ON, and at time t2 when the temperature sensor 25 detects the first set temperature T1, the surface heater 23 is turned OFF. The Peltier element 21 is turned ON at the same time as or slightly after time t2 when the surface heater 23 is turned OFF. When predetermined time S1 is short, the Peltier element 21 is turned ON as the same time as time t2, and when the predetermined time S1 is long, the Peltier element 21 is turned ON later than time t2.

By turning the surface heater 23 OFF and Peltier element 21 ON by the control section 81, temperature of the inspection chip 60 rapidly drops (R2). At time t3 when the temperature sensor 25 detects second set temperature T2, the Peltier element 21 is turned OFF.

When detection temperature detected by the temperature sensor 25 detects the second set temperature T2, the control section 81 feedback controls to turn the surface heater 23 ON/OFF so that the detection temperature becomes equal to the second set temperature T2 in a state where the Peltier element 21 is OFF, thereby maintaining the second set temperature T2 for predetermined time S2. Here, the predetermined time S2 is stored in the storage 82, and the time keeping operation of the timekeeper 83 is started when the second set temperature T2 is detected. If the timekeeper 83 keeps time of the predetermined time S2, the control section 81 turns the surface heater 23 and starts the second cycle.

In this embodiment, the surface heater 23 heats the inspection chip 60 and the Peltier element 21 cools the surface heater 23. Especially according to this, the first set temperature T1 can swiftly be shifted to the second set temperature T2, and the polymerase chain reaction can be carried out in a short time.

According to the embodiment, not only by turning the surface heater 23 OFF but also by forcibly cooling the surface heater 23 by the Peltier element 21, the first set temperature T1 can swiftly be shifted to the second set temperature T2.

Further, in the embodiment, when the detection temperature detected by the temperature sensor 25 detects the second set temperature T2, the surface heater 23 is feedback controlled in the state where the Peltier element 21 is OFF. According to this, since the second set temperature T2 is maintained for the predetermined time S2, hunting can be made small and stable control can be carried out.

Another embodiment of the thermocycling inspection device of the present invention will be described below.

Figure 13:
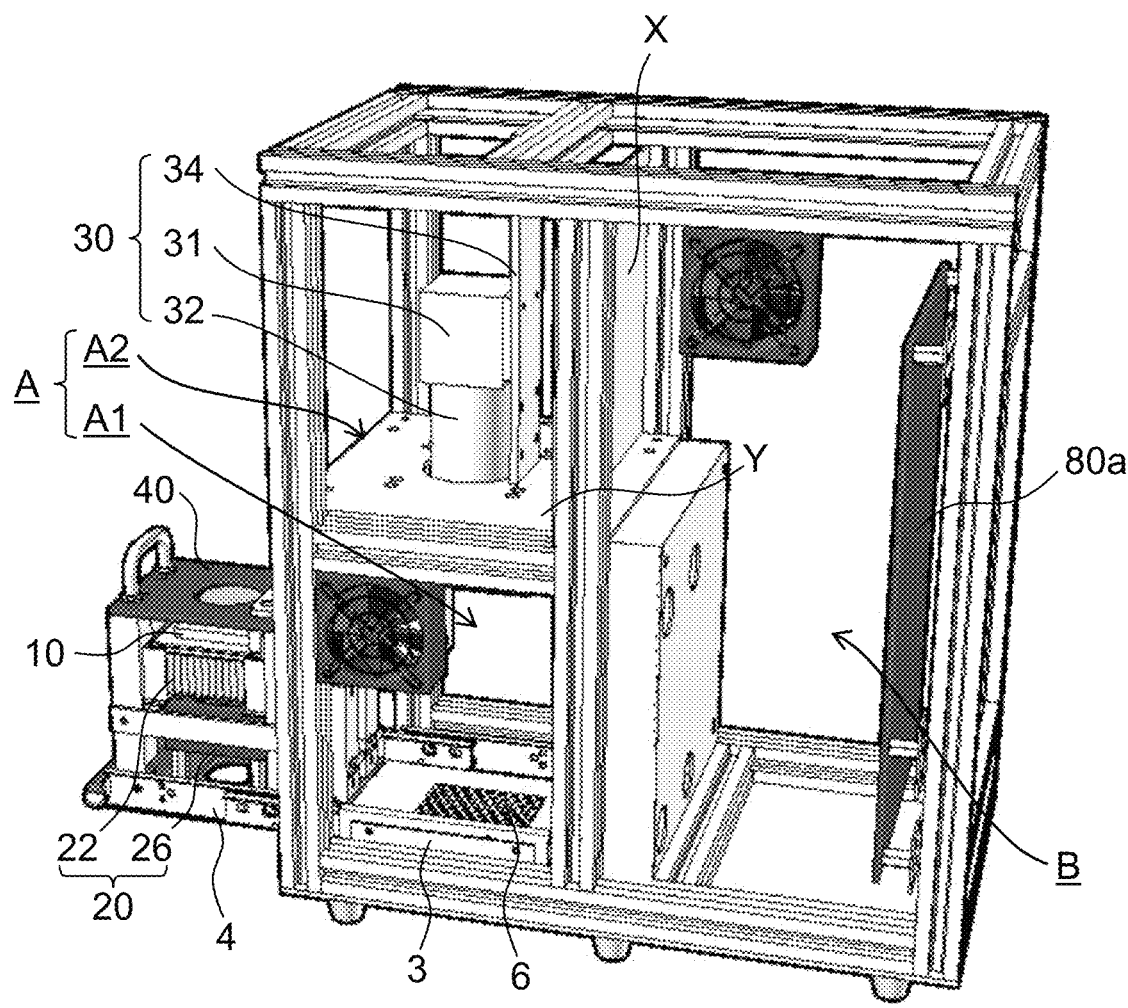
FIG. 13 is a perspective view showing an essential layout configuration in a casing of a thermocycling inspection device according to another embodiment of the present invention.
Figure 14:
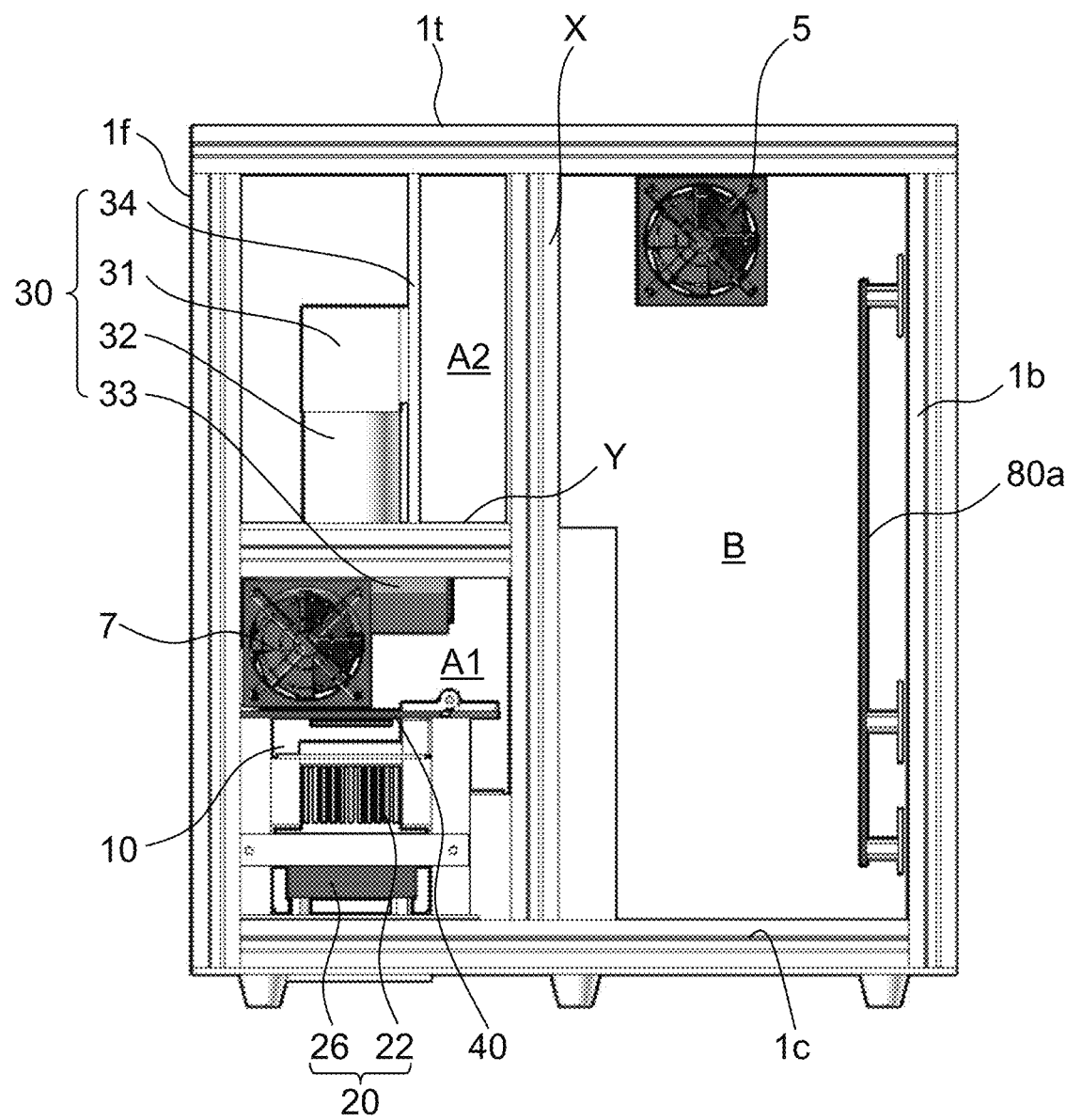
FIG. 14 is a side view showing an essential portion of the thermocycling inspection device.
Figure 15:
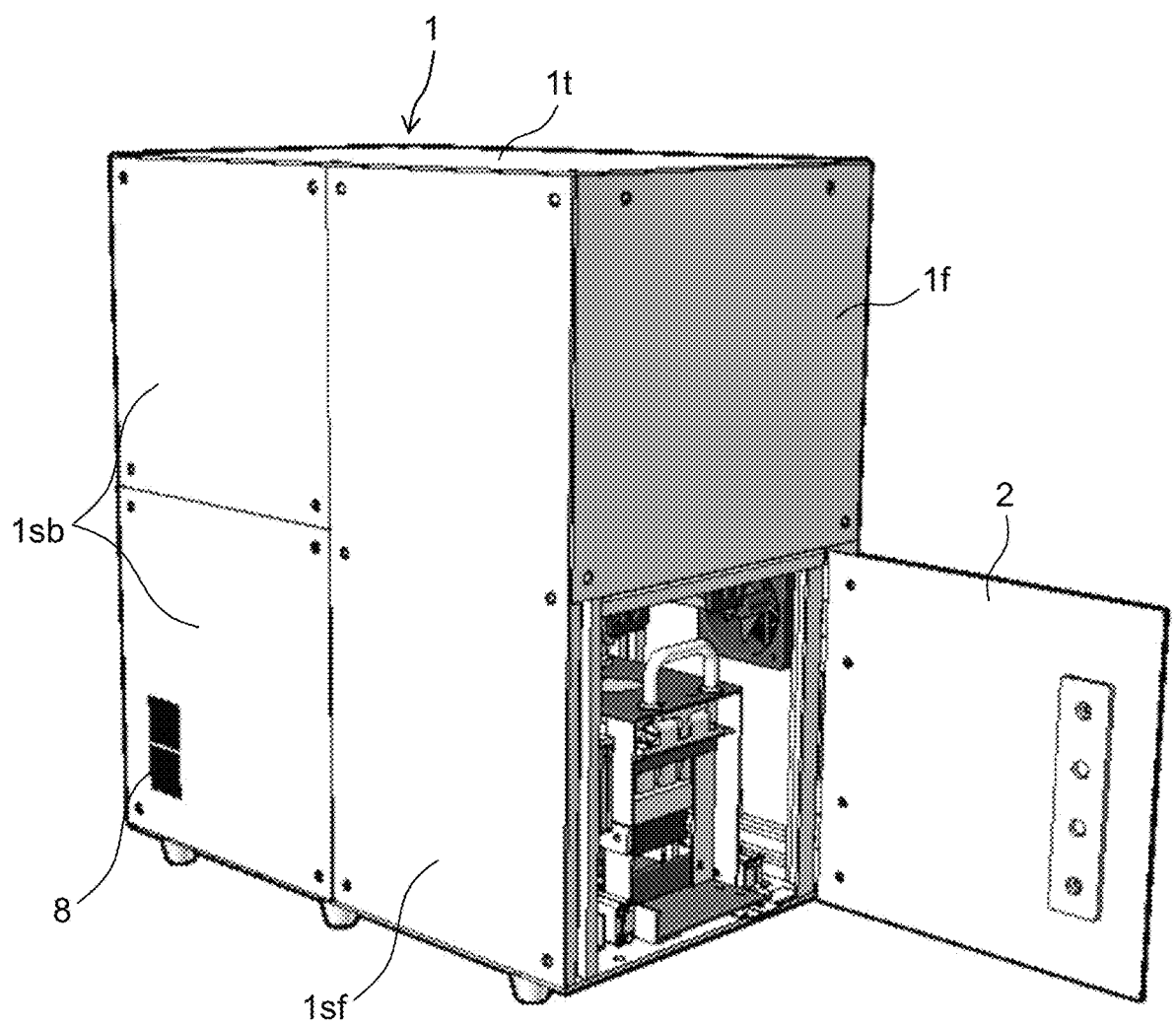
FIG. 15 is a perspective view showing an exterior appearance of the thermocycling inspection device.

FIG. 13 is a perspective view showing an essential layout configuration in a casing of the thermocycling inspection device according to the other embodiment, FIG. 14 is a side view showing an essential portion of the thermocycling inspection device, and FIG. 15 is a perspective view showing an exterior appearance of the thermocycling inspection device. FIGS. 13 and 14 show a state where an outer cover which covers the casing is removed. Explanation of the same configurations and functions as those of the previous embodiment will be omitted and characteristic configurations of this embodiment will be described below.

As shown in FIGS. 13 and 14, an interior of the casing 1 is divided in a front space A and a rear space B by a divider X. The front space A is divided into a lower front space A1 and an upper front space A2 by a divider Y.

A holder-accommodating space 10, a thermocycling section 20, lighting LEDs 33, a tip end of a camera lens 32 and a holder-pressing lid 40 are accommodated in the lower front space A1. A camera 31, portions of the camera lens 32 expect its tip end, and a holding material 34 are accommodated in the upper front space A2. A printed substrate (control section) 80a which controls a Peltier element and a surface heater based on detection temperature detected by a temperature sensor is accommodated in the rear space B. It is preferable that the printed substrate 80a is mounted on a position separated from the divider X through a space and is especially mounted on a rear surface outer cover 1b.

An outer cover (not shown) which forms the lower front space A1 is provided with a heat sink-exhaust fan 7 through which air in the lower front space A1 is discharged. The heat sink-exhaust fan 7 is disposed at a position which is the same height as the heat sink 22 or at a position higher than the heat sink 22. By disposing the heat sink-exhaust fan 7 at an upper portion of the lower front space A1, high temperature air in the lower front space A1 can efficiently be discharged. The heat sink-exhaust fan 7 is provided at a position where a phantom axis of a rotation axis (fan center) of the heat sink-exhaust fan 7 does not pass through a center of the fluorescence detection window (not shown) of the holder-pressing lid 40, more preferably, at a position where this phantom axis does not pass through a surface of projection of the fluorescence detection window of the holder-pressing lid 40. That is, by setting the heat sink-exhaust fan 7 away from the fluorescence detection window, a possibility that light from outside of the casing 1 by the opening of the heat sink-exhaust fan 7 enters the holder-accommodating space 10 is lowered, and the holder-accommodating space 10 can be brought into a dark room.

An outer cover (not shown) which forms the rear space B is provided with the cooling fan 5 which discharges air in the rear space B. The cooling fan 5 is disposed at an upper portion of the printed substrate 80a or at a position higher than the printed substrate 80a. By disposing the cooling fan 5 at an upper portion of the rear space B, high temperature air in the rear space B can efficiently be discharged.

As shown in FIGS. 14 and 15, a front surface of the casing 1 is covered with a front surface outer cover if and a front door 2, both side surfaces of the casing 1 are covered with a rear side surface outer cover 1sb and a front side surface outer cover 1sf, an upper surface of the casing 1 is covered with an upper surface outer cover it, a lower surface of the casing 1 is covered with a lower surface outer cover 1c, and a rear surface of the casing 1 is covered with a rear surface outer cover 1b.

As shown in FIG. 15, a rear space intake port 8 is provided in an outer cover which forms the rear space B, especially below the rear side surface outer cover 1sb.

According to this configuration, in the lower front space A1, air is sucked from an intake port 6 into the casing 1 by a fan 26. Heat of air sucked from the intake port 6 is absorbed by a heat sink 22. Air whose heat is absorbed by the heat sink 22 is forcibly discharged outside from the casing 1 by a heat sink-exhaust fan 7. Therefore, it is possible to enhance the cooling effect of the heat sink 22 and to constantly maintain temperature in the front space A. Further, it is possible to prevent temperature in the upper front space A2 from becoming high.

In the rear space B, air is sucked from the rear space intake port 8 into the casing 1 by the cooling fan 5. Air sucked into the rear space B is discharged outside of the casing 1 from a suction cooling fan 5.

As described above, in the thermocycling inspection device of the present invention, the thermocycling section 20 includes the Peltier element 21, the heat sink 22 disposed on the one surface 21a of the Peltier element 21, the surface heater 23 disposed on the other surface 21b of the Peltier element 21, and the cover plate 24 which covers the surface heater 23 and the other surface 21b of the Peltier element 21. The holder-accommodating space 10 is formed in the thermocycling inspection device to cover the cover plate 24. The opening 24a capable of abutting the chip-accommodating saucer 51 of the chip holder 50 against the surface heater 23 is formed in the cover plate 24. The surface heater 23 heats the inspection chip 60 accommodated in the chip-accommodating saucer 51.

According to the present invention, the heat sink 22 disposed on the one surface 21a of the Peltier element 21 can control the temperature of the Peltier element 21 to a stable value. The surface heater 23 can heat the inspection chip 60. By disposing the surface heater 23 on the other surface 21b of the Peltier element 21, the Peltier element 21 can cool the surface heater 23 and thus, short time cyclic temperature variation can be realized, and the polymerase chain reaction can stably be carried out.

Further, in the thermocycling inspection device of the invention, since the temperature sensor 25 is disposed between the surface heater 23 and the chip-accommodating saucer 51, it is possible to more precisely detect the temperature of the inspection chip 60, and the polymerase chain reaction can stably be carried out.

In the chip holder 50 of the invention, since the recess 51d is provided in the central portion of the chip-accommodating saucer 51, it is possible to prevent specimen liquid charged from the sample introducing port 62 from flowing out into the chip-accommodating saucer 51.

Although the inspection chip 60 which fixes reagent to the sample flow passages 63 is accommodated in the chip holder 50 in the invention, it is also possible to use an inspection chip 60 which does not fix the reagent.

INDUSTRIAL APPLICABILITY

By using the thermocycling inspection device and the inspection chip of the present invention, it is possible to carry out an operation from extraction of specimen to determination of a result within 15 minutes.

The invention claimed is:

1. A thermocycling inspection device comprising: an inspection chip having a sample introducing port and a sample discharge port in a central portion of the inspection chip, and a plurality of sample flow passages radially extending from the sample introducing port a chip holder, the inspection chip configured to fix a reagent to the plurality of sample flow passages by capillary action, the inspection chip is accommodated in the chip holder, and
 a specimen is inspected by polymerase chain reaction using the chip holder, and
  a thermocycler that heats and cools the inspection chip,
  a detector that takes a picture of the inspection chip,
  the thermocycler having an upper surface, wherein the chip holder is disposed on the upper surface of the thermocycler,
  a pair of slide rails that moves the thermocycler including the chip holder such that an optical axis of the detector and an optical axis of the sample introducing port match with each other when the thermocycler heats or cools the inspection chip or when a picture of the inspection chip is taken by the detector,
 wherein the chip holder further includes:
  a chip-accommodating saucer configured to accommodate the inspection chip therein,
  a holder configured to hold the chip-accommodating saucer at a central portion of the holder, the holder having an upper surface comprising a ring-shaped recess, positioning recesses and fixing holes, and
  a chip-pressing device configured to press the inspection chip accommodated in the chip-accommodating saucer against the chip-accommodating saucer, and the ring-shaped recess is formed around an outer periphery of the chip-accommodating saucer, the positioning recesses are continuous with the ring-shaped recess, each of the fixing holes are formed in a portion of a positioning recess of the positioning recesses, the chip-pressing device comprising a ring portion, positioning legs, fixing projections and chip pressing legs, the ring portion is mounted on the ring-shaped recess, the positioning legs are mounted on the positioning recesses, each of the fixing projections is fitted into a corresponding fixing hole of the fixing holes, the ring portion is mounted on the ring-shaped recess and the positioning legs are mounted on the positioning recesses, thereby the chip-pressing device is positioned on the holder, and the fixing projections are fitted into the fixing holes, the chip-pressing device is fixed to the holder.

2. The thermocycling inspection device according to claim 1, wherein the thermocycler includes:
a Peltier element,
a heat sink disposed on one surface of the Peltier element,
a heater disposed on other surface of the Peltier element, and
a cover plate covering the heater and the other surface of the Peltier element,
the cover plate having an opening, wherein the opening of the cover plate is configured to facilitate the chip-accommodating saucer of the chip holder to abut against the heater, and
the inspection chip accommodated in the chip-accommodating saucer is heated by the heater.

3. The thermocycling inspection device according to claim 2, wherein a temperature sensor is disposed between the heater and the chip-accommodating saucer.

4. The thermocycling inspection device according to claim 2, further comprising a holder-pressing lid, which covers the chip holder disposed in the holder-accommodating space, wherein
a fluorescence detection window is formed in the holder-pressing lid,
a transparent substrate is provided on the holder-pressing lid, and
the transparent substrate covers the fluorescence detection window and presses the chip holder.

5. The thermocycling inspection device according to claim 1, wherein the thermocycler includes;
a Peltier element,
a heater, and
a temperature sensor for detecting temperature of the inspection chip, and
the heater heats the inspection chip, and
the Peltier element cools the heater.

* * * * *